(12) United States Patent
Almutairi et al.

(10) Patent No.: US 9,333,264 B2
(45) Date of Patent: May 10, 2016

(54) BIOCOMPATIBLE POLYMERIC NANOPARTICLES DEGRADE AND RELEASE CARGO IN RESPONSE TO BIOLOGICALLY RELEVANT LEVELS OF HYDROGEN PEROXIDE

(71) Applicant: The Regents of the University of California, Oakland, CA (US)

(72) Inventors: Adah Almutairi, La Jolla, CA (US); Caroline De Gracia Lux, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/199,876

(22) Filed: Mar. 6, 2014

(65) Prior Publication Data
US 2014/0255311 A1  Sep. 11, 2014

Related U.S. Application Data

(60) Provisional application No. 61/773,772, filed on Mar. 6, 2013.

(51) Int. Cl.
| | |
|---|---|
| *A61K 8/00* | (2006.01) |
| *A61K 47/34* | (2006.01) |
| *C08G 79/08* | (2006.01) |
| *A61K 31/337* | (2006.01) |
| *A61K 31/573* | (2006.01) |
| *A61K 47/48* | (2006.01) |
| *A61K 9/00* | (2006.01) |
| *A61K 9/08* | (2006.01) |
| *A61K 9/51* | (2006.01) |
| *A61K 31/69* | (2006.01) |
| *A61K 9/14* | (2006.01) |

(52) U.S. Cl.
CPC ............... *A61K 47/34* (2013.01); *A61K 9/0048* (2013.01); *A61K 9/08* (2013.01); *A61K 9/5153* (2013.01); *A61K 31/337* (2013.01); *A61K 31/573* (2013.01); *A61K 31/69* (2013.01); *A61K 47/482* (2013.01); *C08G 79/08* (2013.01); *A61K 9/14* (2013.01); *A61K 9/141* (2013.01); *C08G 2261/1644* (2013.01)

(58) Field of Classification Search
None
See application file for complete search history.

(56) References Cited

U.S. PATENT DOCUMENTS 8,758,778 B2  6/2014  Almutairi et al.
8,828,383 B2  9/2014  Almutairi et al.

OTHER PUBLICATIONS de Gracia Lux. "Biocompatible Polymeric Nanoparticles Degrade and Release Cargo in Response to Biologically Relevant Levels of Hydrogen Peroxide" J. Am. Chem. Soc. 2012, 134, pp. 15758-15764.*
Haba, K., et al., Single-Triggered Trimeric Prodrugs, Angew. Chem. 2005, 117,726-730.
Goodwin, A.P., et al., "Synthetic Micelle Sensitive to IR Light via a Two-Photon Process", J. Am. Chem. Soc. 2005, 127, 9952-9953, published online Jun. 25, 2005.
Mynar, J.L, et al., "Two-photon degradable supramolecular assemblies of linear-dendritic copolymers", Chem Commun. (Camb.) 2007, 2081-2082.
Jourden, J.L.M. and Cohen, S.M., "Hydrogen Peroxide Activated Matrix Metalloproteinase Inhibitors: A Prodrug Approach," Angew Chem Int Ed Engl., Sep. 10, 2010; 49(38): 6795-6797.
Jourden, J.L.M., et al., "Investigation of self-immolvative linkers in the design of hydrogen peroxide activated metalloprotein inhibitors", Chem Commun. (Camb.) Jul. 28, 2011; 47(28): 7968-7970.
Murthy, N., et al., "A macromolecular delivery vehicle for protein-based vaccines: Acid-degradable protein-loaded microgels", Proc. Nat. Acad. Sci. (PNAS) Apr. 29, 2003; 100(9): 4995-5000.
de Gracia Lux, C., et al., "Biocompatible Polymeric Nanoparticles Degrade and Release Cargo in Response to Biologically Relevant Levels of Hydrogen Peroxide", J. Amer. Chem. Soc.; Sep. 4, 2012; 134(38):15758-15764.
Van de Bittner, G., et al., "In vivo imaging of hydrogen peroxide production in a murine tumor model with chemoselective bioluminescent reporter", Proc. Nat. Acad. Sci. (PNAS); Dec. 14, 2010; 107 (50): 21316-21321.
Wang, W., et al., "Self-Immolative Polymers", Angew. Chem Int'l. Ed.; 2008, 47; 7804-7806.

* cited by examiner

*Primary Examiner* — James Rogers
(74) *Attorney, Agent, or Firm* — Eleanor Musick

(57) ABSTRACT

Disclosed are compositions and synthesis methods that pertain to biocompatible polymeric capsules capable of undergoing backbone degradation and cargo release upon exposure to biologically relevant concentrations of hydrogen peroxide (50-100 μM of $H_2O_2$). In the invention, bio-responsive polyester bearing boronic ester triggers groups that degrade upon exposure to low concentrations of $H_2O_2$. The degradation is induced by transformation of a boronic ester to a phenol, which undergoes a quinone methide rearrangement to break down the polyester backbone.

7 Claims, 19 Drawing Sheets

(SCHEME 1)

(SCHEME 2)

FIG. 3A
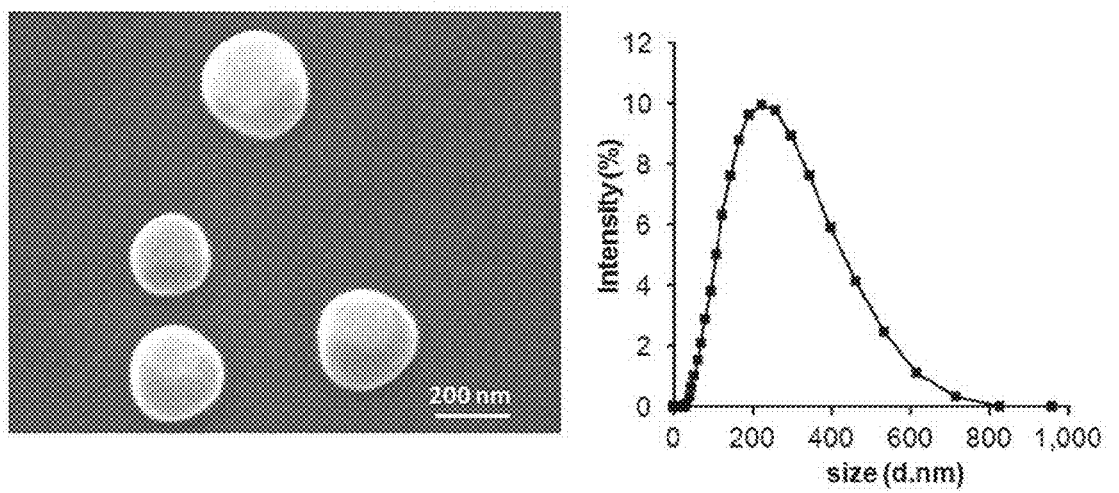
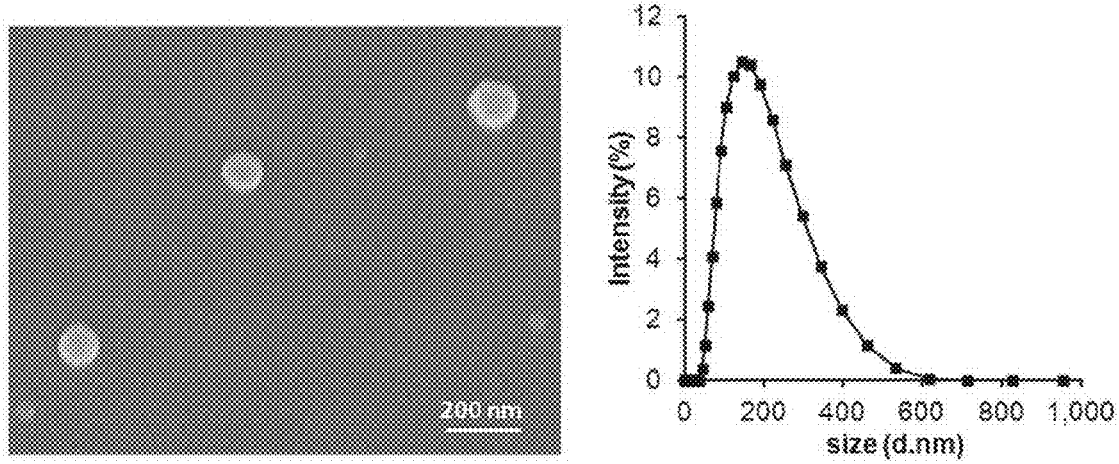
FIG. 3B

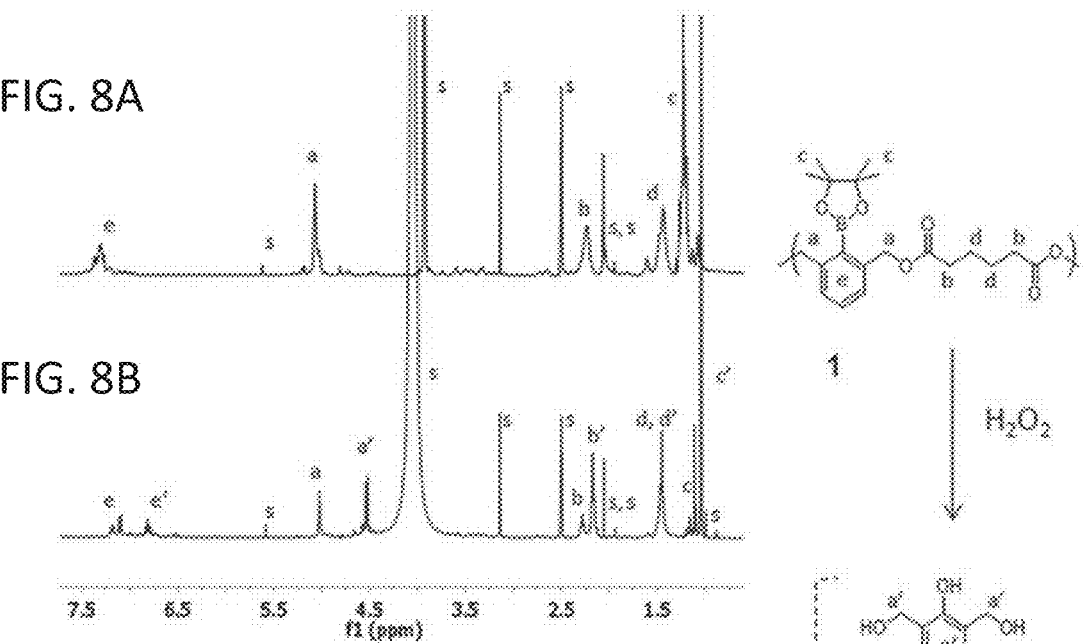
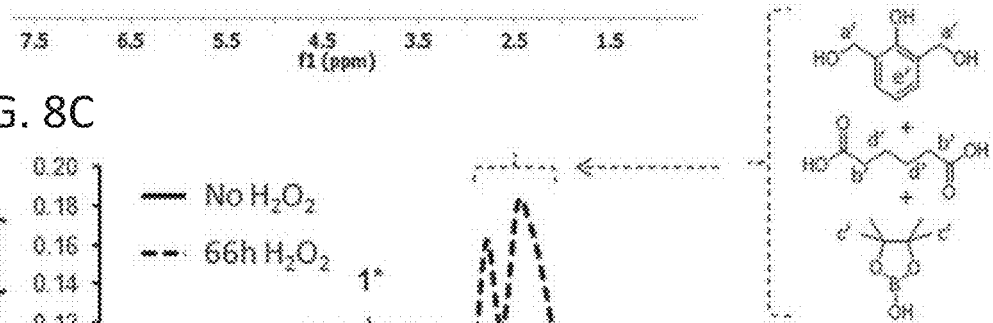
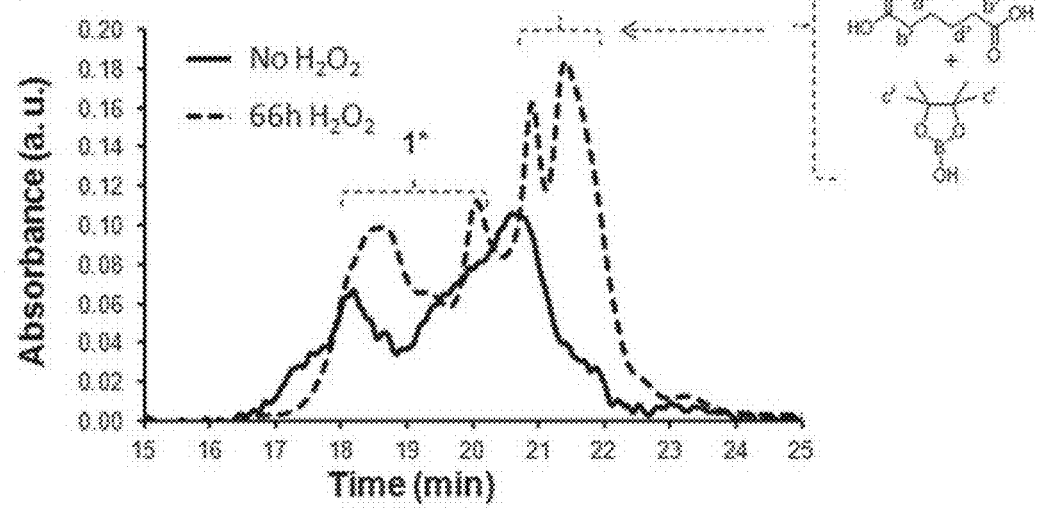
FIG. 8A
FIG. 8B
FIG. 8C

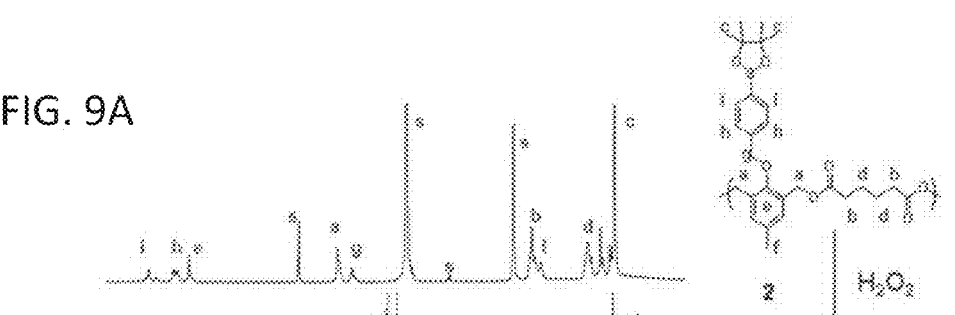
FIG. 9A
FIG. 9B
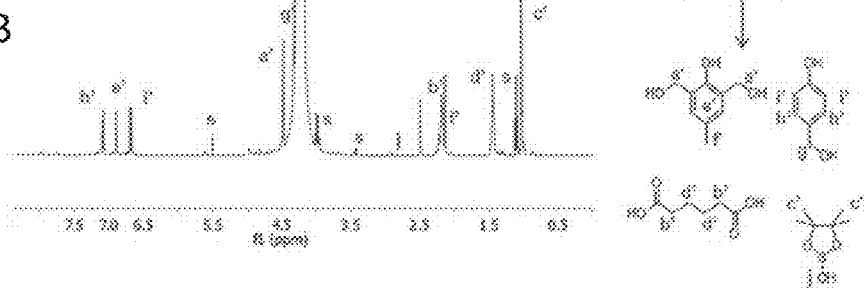
FIG. 9C
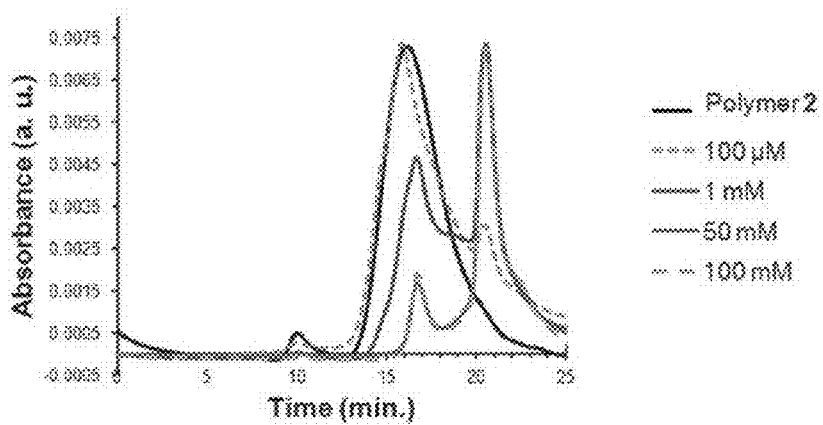
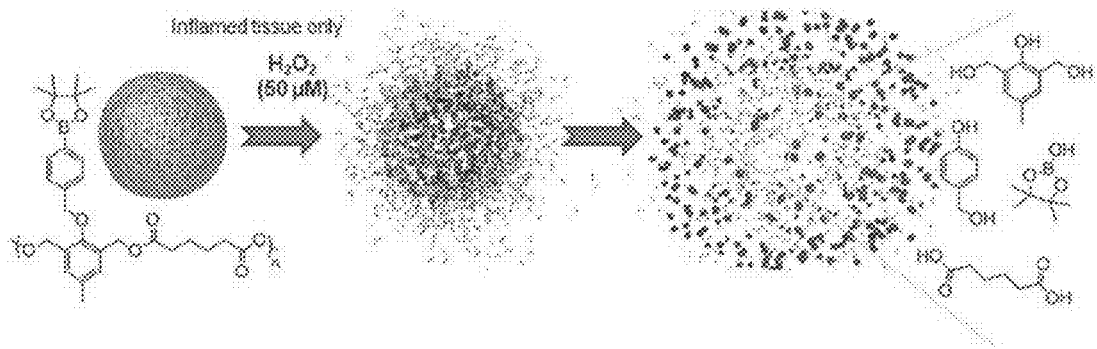
FIG. 10

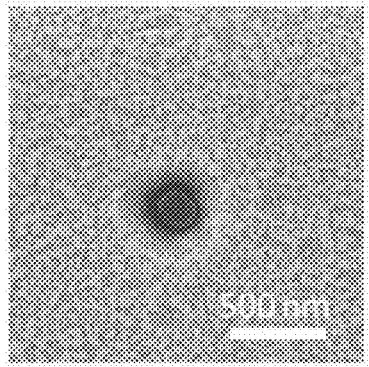 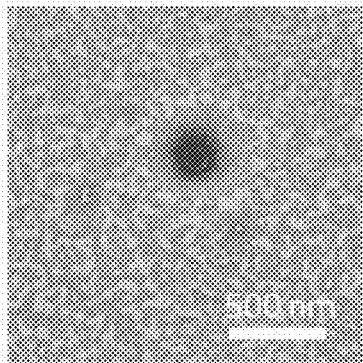 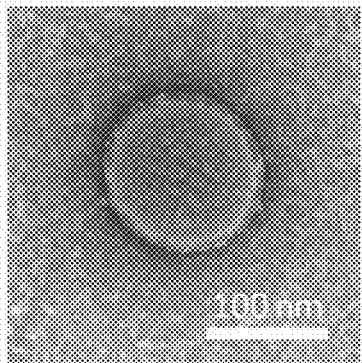
FIG. 11A　　　　　　FIG. 11B　　　　　　FIG. 11C
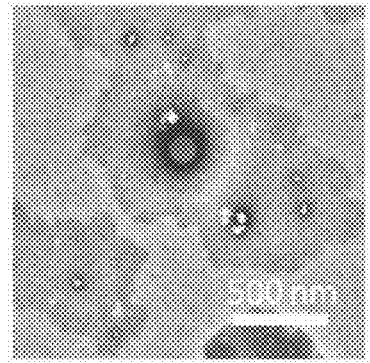 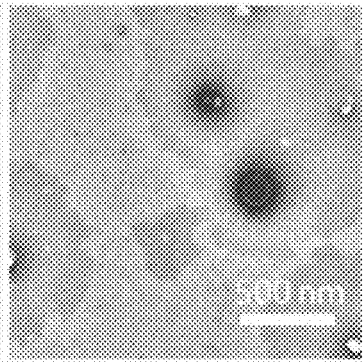 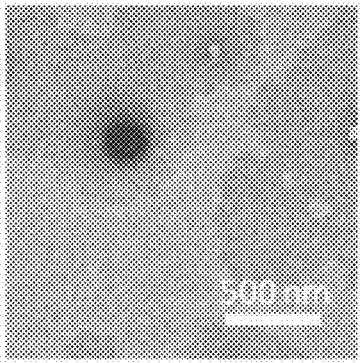
FIG. 12A　　　　　　FIG. 12B　　　　　　FIG. 12C

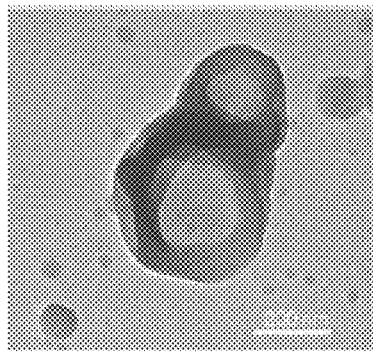 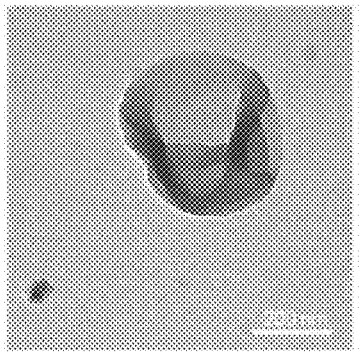 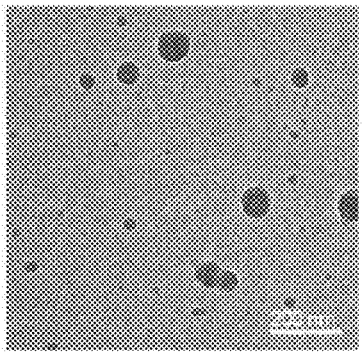
FIG. 19A FIG. 19B FIG. 19C
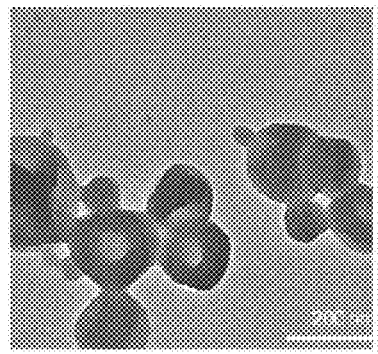 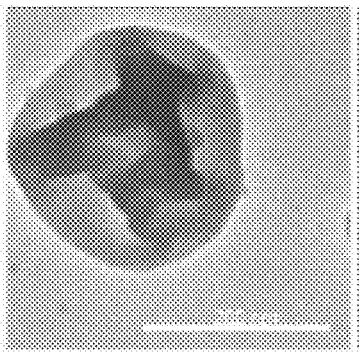 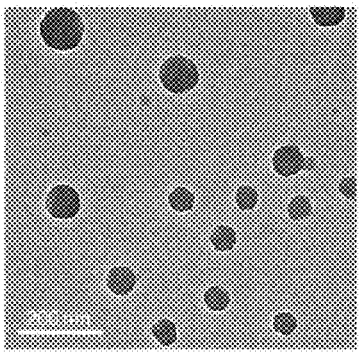
FIG. 20A FIG. 20B FIG. 20C

BIOCOMPATIBLE POLYMERIC NANOPARTICLES DEGRADE AND RELEASE CARGO IN RESPONSE TO BIOLOGICALLY RELEVANT LEVELS OF HYDROGEN PEROXIDE

RELATED APPLICATIONS

This application claims the benefit of the priority of U.S. Provisional Application No. 61/773,772, filed Mar. 6, 2013, which is incorporated herein by reference in its entirety.

GOVERNMENT RIGHTS

This invention was made with government support under Grant No. 1DP2OD006499-01 awarded by the National Institutes of Health. The government has certain rights in the invention.

FIELD OF THE INVENTION

The present invention relates to nanoparticles formulated from polymers that are biodegradable in $H_2O_2$ and to biodegradable $H_2O_2$-triggered release systems that can degrade into small molecules, release their cargo, and are easily cleared by the body.

BACKGROUND OF THE INVENTION

Oxidative stress is caused predominantly by accumulation of hydrogen peroxide and distinguishes inflamed tissue from healthy tissue. Hydrogen peroxide could potentially be useful as a stimulus for targeted drug delivery to diseased tissue. However, current polymeric systems are not sensitive to biologically relevant concentrations of $H_2O_2$ (50-100 µM). The contribution of oxidative stress and reactive oxygen species (ROS) to the development of numerous diseases has resulted in a research focus to create ROS-specific detection systems and ROS-responsive micro-detection systems or nanocarriers. See, e.g., Li, C. H., et al, *Macromolecules* 2011, 44, 429; Van de Bittner, G. C., et al., *J. Proc. Natl. Acad. Sci. U.S.A.* 2010, 107, 21316; Sella, E., et al, *J. Am. Chem. Soc.* 2010, 132, 3945; Srikun, D. et al, *J. Am. Chem. Soc.* 2008, 130, 4596; Lee, D., et al, *Nat. Mater.* 2007, 6, 765; Chang, M. C. Y., et al, *J. Am. Chem. Soc.* 2004, 126, 15392; Yu, S. S., et al, *Biomacromolecules* 2011, 12, 4357; Broaders, K. E., et al, *J. Am. Chem. Soc.* 2011, 133, 756; Wilson, D. S., et al, *Nat. Mater.* 2010, 9, 923; Rehor, A., et al, *Langmuir* 2005, 21, 411; Napoli, A., et al, *Nat. Mater.* 2004, 3, 183; Khutoryanskiy, V., et al, *Pure Appl. Chem.* 2008, 80, 1703; Allen, B. L., et al, *ACS Nano* 2011, 5, 5263.

Oxidative stress is a condition in which the balance of oxidative and reducing species within cellular environments has been disturbed. Once out of balance, ROS such as superoxide, hydrogen peroxide, and hydroxide radicals can damage cellular components. Geronikaki, A. A., et al, *Comb. Chem. High Throughput Screening* 2006, 9, 425.

Although some ROS are key to cell signaling and defense mechanisms, these chemicals also contribute to various diseases. See, e.g., Finkel, T. *Curr. Opin. Cell Biol.* 2003, 15, 247; Cachofeiro, V., et al., *J. Kidney Int.* 2008, S4; Drechsel, D. A., et al, *Free Radic. Biol. Med.* 2008, 44, 1873; Liou, G. Y., et al, *Free Radical Res.* 2010, 44, 479.

Methods of selective delivery of therapeutic and diagnostic reagents to sites undergoing oxidative stress would prove useful for the numerous diseases characterized by high concentrations of ROS. Polymer-based nano- and microparticles are especially useful because they can be tailored to degrade upon encountering certain stimuli, such as enzymatic removal of a protecting group, pH, light, and $H_2O_2$. See, e.g., Esser-Kahn, A. P., et al, *Macromolecules* 2011, 44, 5539; Seo, W., et al, *J. Am. Chem. Soc.* 2010, 132, 9234; Dewit, M. A., et al., *J. Am. Chem. Soc.* 2009, 131, 18327; Murthy, N., et al, *J. Proc. Natl. Acad. Sci. U.S.A.* 2003, 100, 4995; Murthy, N., et al, *J. Am. Chem. Soc.* 2002, 124, 12398; Sankaranarayanan, J., et al, *ACS Nano* 2010, 4, 5930; Goodwin, A. P., et al, *J. Am. Chem. Soc.* 2005, 127, 9952; Fomina, N., et al, *J. Am. Chem. Soc.* 2010, 132, 9540; Sella, E., et al, *J. Am. Chem. Soc.* 2010, 132, 3945; Lee, D., et al, *Nat. Mater* 2007, 6, 765; Rehor, A., et al, *Langmuir* 2005, 21, 411; Avital-Shmilovici, et al, *Bioorg. Med. Chem.* 2010, 18, 3643; Heffernan, M. J., et al, *Bioconjugate Chem.* 2005, 16, 1340.

Upon encapsulation, nanoparticles can provide improved pharmacokinetics, as the therapeutic drug is protected from the physiological environment and selected release allows for lower drug loading through effective site delivery. See, e.g., Petros, R. A., et al, *Nat. Rev. Drug Discovery* 2010, 9, 615. There are few, if any, polymeric systems able to undergo degradation and cargo release on encountering biologically relevant (50-100 µM) $H_2O_2$ concentrations. One important study showed a polymeric carrier responsive to 1 mM $H_2O_2$ in a useful time frame using dextran reversibly modified with aryl boronic esters, this system utilized a carbonate ester linkage, and took advantage of a solubility switching mechanism to release its payload. See, Broaders, K. E., et al, *J. Am. Chem. Soc.* 2011, 133, 756.

Notably, this study also demonstrated the advantage of such boronic ester stabilized nanomaterials for promoting immune activation by antigen-presenting cells.

SUMMARY OF THE INVENTION

Disclosed are compositions and synthesis methods that pertain to biocompatible polymeric capsules capable of undergoing backbone degradation and cargo release upon exposure to biologically relevant concentrations of hydrogen peroxide (50-100 µM of $H_2O_2$). In the invention, a bio-responsive polyester bearing boronic ester triggers groups that degrade upon exposure to low concentrations of $H_2O_2$. The degradation is induced by transformation of a boronic ester to a phenol, which undergoes a quinone methide rearrangement to break down the polyester backbone.

Applications are in the field of targeted drug delivery to diseased tissue (e.g., associated with inflammatory diseases like chronic obstructive pulmonary disease and rheumatoid arthritis), using hydrogen peroxide as trigger. Advantages of the invention are good synthetic accessibility and hydrolytic stability, fast $H_2O_2$ triggered cleavage kinetics, good biocompatibility, and the formation of only small degradation molecules that should be easily cleared by the body.

Two polymeric structures developed and disclosed herein differ with respect to the linkage between the boronic ester group and the polymeric backbone: either direct linkage (Polymer 1) or linkage via a benzyl ether (Polymer 2). Both polymers are stable in aqueous solution at normal pH, and exposure to peroxide induces the removal of the boronic ester protecting groups at physiological pH and temperature, revealing phenols along the backbone, which undergo quinone methide rearrangement to lead to polymer degradation. In some embodiments, faster backbone degradation was observed for Polymer 2 over Polymer 1 by NMR and GPC.

Nanoparticles were formulated from the novel materials disclosed herein to analyze their oxidation triggered release properties. While nanoparticles formulated from Polymer 1 only released 50% of the reporter dye after exposure to 1 mM $H_2O_2$ for 26 h, nanoparticles formulated from Polymer 2 did so within 10 h and were able to release their cargo selectively in biologically relevant concentrations of $H_2O_2$. Nanoparticles formulated from Polymer 2 showed a two-fold enhancement of release upon incubation with activated neutrophils while controls showed non-specific response to ROS producing cells.

In one embodiment, polymers are used to encapsulate small hydrophobic molecules and measure their release upon exposure to biologically relevant oxidative conditions. This approach represents an addition to the very small toolbox of systems with the potential to target drug delivery to oxidative conditions.

In some embodiments, the disease, disorder or condition is Arthritis; Keshan Disease; Myocardial Infarction; Atherosclerosis; or Arterial Sclerosis.

In some embodiments, the disease, disorder or condition is Asthma; Acute Respiratory Distress Syndrome (ARDS); Hyperoxia or Pulmonary Edema.

In some embodiments, the disease, disorder or condition is Inflammatory Bowel Disease (IBD); Crohn's Disease; Ischemic Bowel Disease; Cancer; Inflammatory Immune Response; Diabetes; Injury Ischemia Reflow Injury; Vasospasm; Hemolytic Anemia; Progeria or Progressive Systemic Sclerosis.

In some embodiments, the disease, disorder or condition is Hepatic Cirrhosis; Renal Graft; Glomerulonephritis and Endotoxin Liver Injury.

In some embodiments, the disease, disorder or condition is Parkinson's disease; Alzheimer's disease; Schizophrenia; Cerebral Edema; Cerebral Infarction; Epilepsy; Bipolar Disorder.

In some embodiments, the disease, disorder or condition is Wrinkling; Baldness; Presbyopia; Cataracts; Hearing loss; Hypertension; or Memory loss.

In some embodiments, the disease, disorder or condition is Glaucoma; Dry Eyes; Degenerative Retinal Damage (ARMD); Neovascular Age-Related Macular Degeneration (AMD); Cataractogenesis; Retinopathy of Prematurity (ROP); Ocular Uveitis; or Cataracts.

In some embodiments, the disease, disorder or condition is Burns, Dermatitis; Psoriasis; Vitiligo, or Androgenic Alopecia.

In various embodiments, provided herein are polymers having the structure

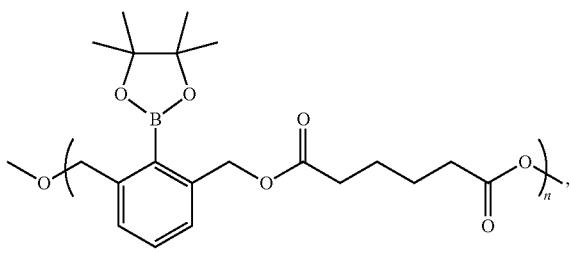

where n is a whole integer between 15 and 25; or

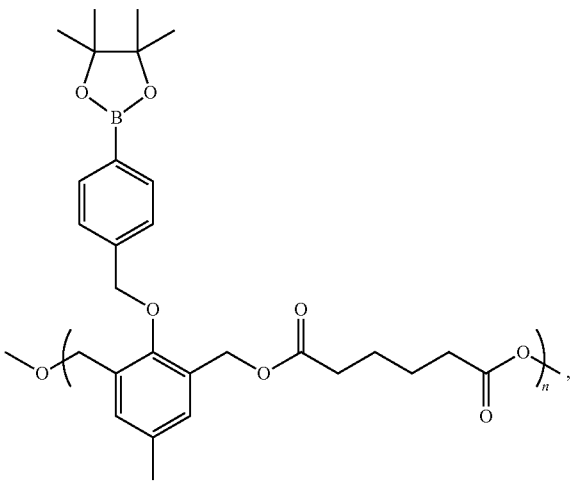

where n is a whole integer between 75 and 100.

In various embodiments, the structure of the polymer is

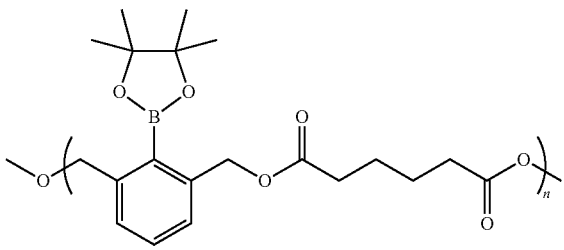

and the polydispersity index (PDI) is about 1.9. In one non-limiting specific embodiments, the molecular weight is about 10623.

In some embodiments, the structure of the polymer is:

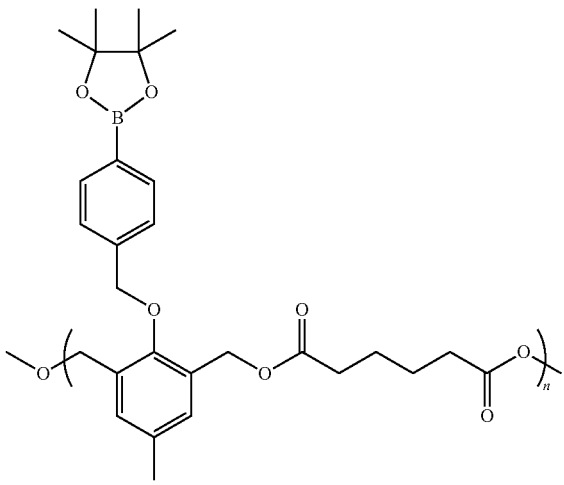

and the polydispersity index (PDI) is about 1.4. In one non-limiting specific embodiment, the molecular weight is about 51.3 kDa.

Also provided herein are pharmaceutical compositions comprising a nanoparticle comprising a polymer having the structure

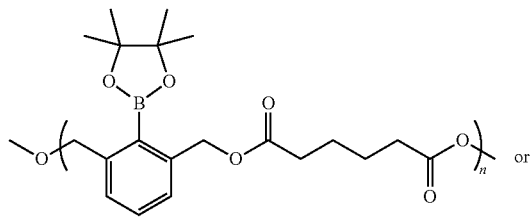 or

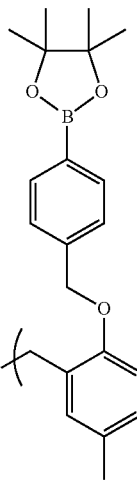

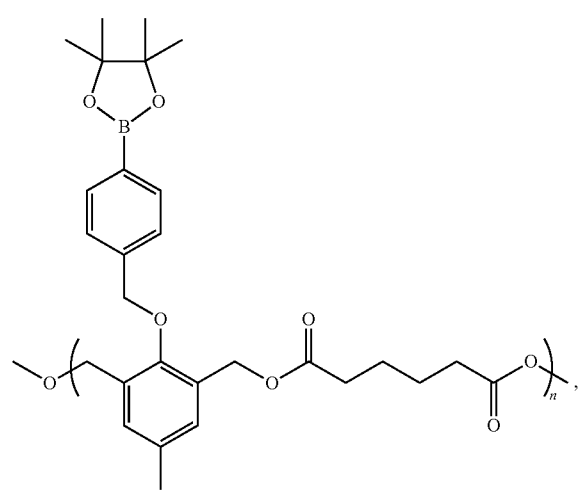

where n is a whole integer between 15-20 and 75-100, respectively; at least one active ingredient; and a pharmaceutically-acceptable excipient. In some specific embodiments, the polymer is

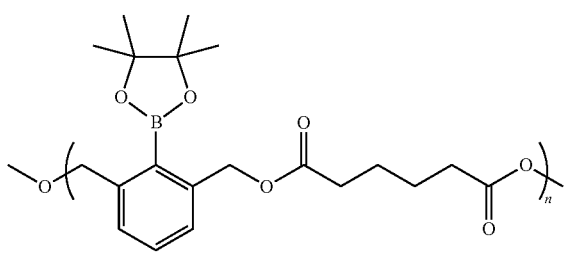

and has a molecular weight between about 10000 and 12000. In one non-limiting specific embodiment, the polymer has a polydispersity index (PDI) of about 1.9 and the molecular weight is about 10623. In other embodiments, the polymer in the pharmaceutical composition is and has a molecular weight between about 50 kDa and 53 kDa. In one non-limiting specific embodiment the polymer has a polydispersity index (PDI) of about 1.4 and the molecular weight is about 51.3 kDa.

In various embodiments of the pharmaceutical compositions described herein, the pharmaceutically-acceptable excipient is a thickener, an oil phase, a surfactant, a preservative, or a pH adjusting agent. In some embodiments, the pharmaceutical composition is a solution, emulsion, cream, ointment, lotion, gel, powder, solid, tincture, paste, vapor, tape, or lotion.

Also provided herein are methods for treating a disease, disorder or visualizing condition characterized by unwanted or excessive oxidative stress in an individual in need thereof, comprising administering to the individual a pharmaceutical composition comprising: a polymer having the structure:

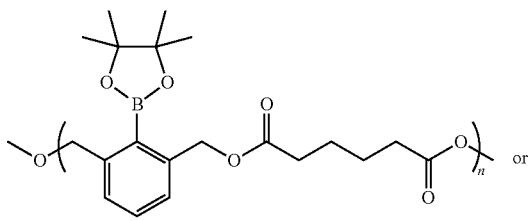 or

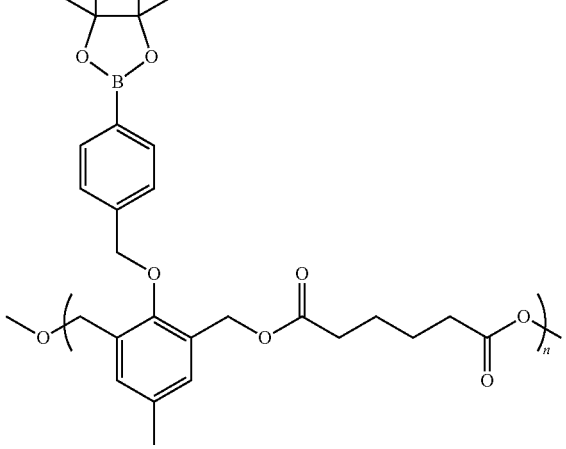

where n is a whole integer between about 15-20 and 75-100, respectively, to form a delivery mechanism; and at least one active ingredient. In one specific embodiment, the polymer is

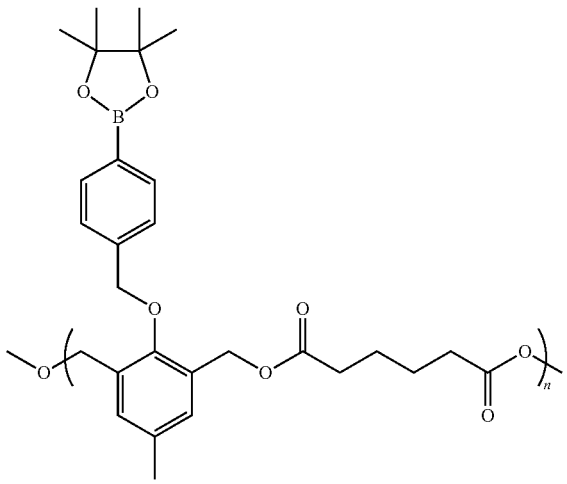

and has a molecular weight of about 51.3 kDa and a polydispersity index (PDI) of about 1.4. In another non-limiting specific embodiment, the polymer is

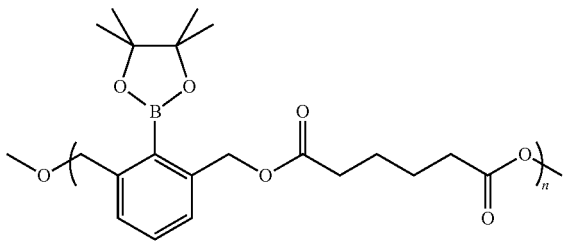

and has a molecular weight of about 10623 and a polydispersity index (PDI) of about 1.9.

In various embodiments the disease, disorder or visualizing condition is Glaucoma; Dry Eyes; Degenerative Retinal Damage (ARMD); Cataractogenesis; Retinopathy of Prematurity (ROP); Ocular Uveitis; Cataracts; Burns; Dermatitis; Psoriasis; Vitiligo, Androgenic Alopecia; arthritis; Keshan Disease; Myocardial Infarction; Atherosclerosis; Arterial Sclerosis; Asthma; Acute Respiratory Distress Syndrome (ARDS); Hyperoxia; Pulmonary Edema; Inflammatory Bowel Disease (IBD); Crohn's Disease; Ischemic Bowel Disease; Cancer; Inflammatory Immune Response; Diabetes; Injury Ischemia Reflow Injury; Vasospasm; Hemolytic Anemia; Progeria; Progressive Systemic Sclerosis; Hepatic Cirrhosis; Renal Graft; Glomerulonephritis; Endotoxin Liver Injury; Parkinson's Disease; Alzheimer's Disease; Schizophrenia; Cerebral Edema; Cerebral Infarction; Epilepsy; Bipolar Disorder; Wrinkling; Baldness; Presbyopia; Cataracts; Hearing loss; Hypertension; or Memory loss.

In some specific embodiments the disease, disorder or visualizing condition being treated is neovascular age-related macular degeneration (AMD). In other specific embodiments, the disease, disorder or visualizing condition is inflammation; chronic obstructive pulmonary disease or vulnerable atherosclerotic plaque. In yet other embodiments, the disease, disorder or visualizing condition is rheumatoid arthritis (RA) and the composition allows for selective anti-inflammatory delivery to inflamed joints.

Provided herein in various embodiments are methods for delivering a diagnostic or therapeutic agent to a patient in need thereof, comprising: forming a delivery mechanism by encapsulating the diagnostic or therapeutic agent into a nanoparticle comprising a polymer having the structure

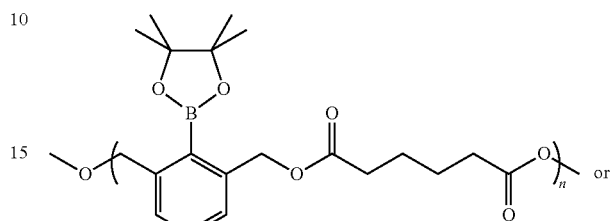

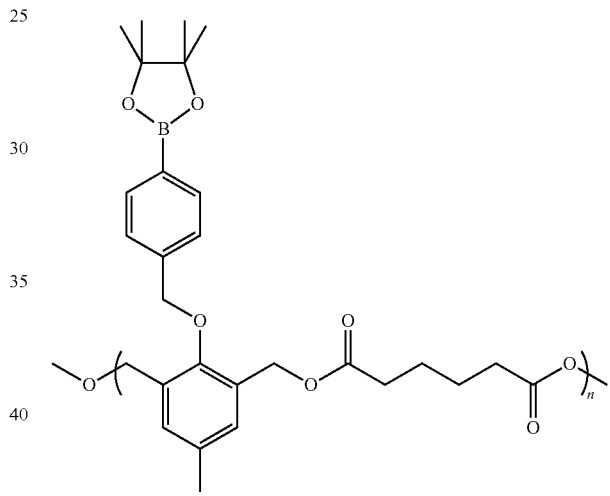

where n is a whole integer between 15-20 and 75-100, respectively; and administering the delivery mechanism to the patient.

In some specific embodiments, the polymer in the nanoparticle is

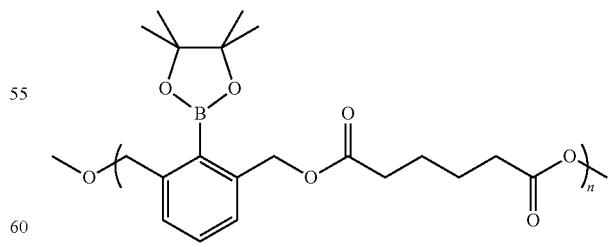

and has a molecular weight between about 10000 and 12000. In one non-limiting specific embodiment, the polymer in the nanoparticle has a polydispersity index (PDI) of about 1.9 and the molecular weight is about 10623. In other embodiments, the polymer in the nanoparticle is

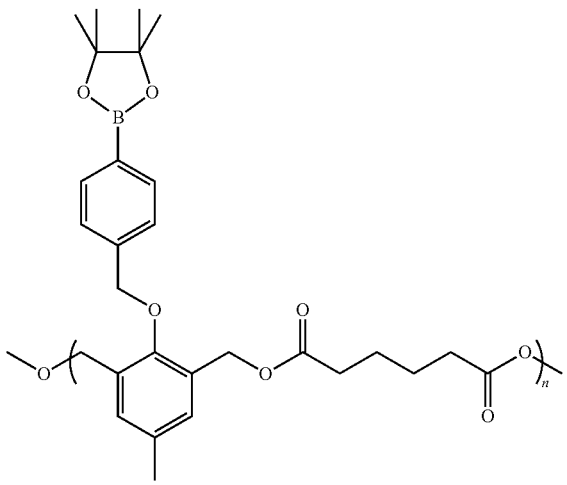

and has a molecular weight between about 50 kDa and 53 kDa. In one non-limiting specific embodiment the polymer in the nanoparticle has a polydispersity index (PDI) of about 1.4 and the molecular weight is about 51.3 kDa.

In various embodiments, the delivery mechanisms described herein release at least 50% of the active ingredient within 72 hours after administration to a patient. In specific embodiments, the delivery mechanisms release at least 50% of the active ingredient within 48 hours, or within 36 hours, or within 24 hours or within 20 hours, or within 10 hours after administration to a patient.

In some embodiments, the delivery mechanisms described herein release between about 10-75% of the active ingredient within 72 hours after administration to a patient. In specific embodiments, the delivery mechanisms described herein release between about 15-70%, or between about 20-65%, or between about 15-55%, or between about 15-50%, or between about 10-50%, or between about 10-40%, or between about 10-30%, or between about 10-25%, or between about 10-15% of the active ingredient within 72 hours after administration to a patient.

In some embodiments, the delivery mechanisms described herein release between about 10-75% of the active ingredient within 48 hours after administration to a patient. In specific embodiments, the delivery mechanisms described herein release between about 15-70%, or between about 20-65%, or between about 15-55%, or between about 15-50%, or between about 10-50%, or between about 10-40%, or between about 10-30%, or between about 10-25%, or between about 10-15% of the active ingredient within 48 hours after administration to a patient.

In some embodiments, the delivery mechanisms described herein release between about 10-75% of the active ingredient within 24 hours after administration to a patient. In specific embodiments, the delivery mechanisms described herein release between about 15-70%, or between about 20-65%, or between about 15-55%, or between about 15-50%, or between about 10-50%, or between about 10-40%, or between about 10-30%, or between about 10-25%, or between about 10-15% of the active ingredient within 24 hours after administration to a patient.

Other features and advantages of the present disclosure will become more readily apparent to those of skill in the art after reviewing the following detailed description and accompanying drawings.

BRIEF DESCRIPTION OF THE FIGURES

The details of the present disclosure, both as to its structure and operation, may be gleaned in part by study of the accompanying drawings, in which like reference numerals refer to like parts.

FIG. 3A and FIG. 3B illustrate characterizations of polymeric particles by SEM and DLS, according to one embodiment. Specifically, FIG. 3A shows Polymer 1 (d=166 nm (standard deviation 5.7), PDI=0.38 (standard deviation 0.07)) and FIG. 3B shows Polymer 2 (d=136 nm (standard deviation 5.4), PDI=0.30 (standard deviation 0.01)).

FIG. 5A and FIG. 5C show the nanoparticles after 72 h of incubation in PBS, and FIG. 5B and FIG. 5D correspond to after 72 h in PBS containing 1 mM $H_2O_2$.

FIG. 8A and FIG. 8B show $^1H$ NMR spectra of Polymer 1 in DMSO-$d_6$, deuterium PBS (8A) without $H_2O_2$ and (8B) incubated with 500 mM $H_2O_2$ after 3 days at 37° C., where "s" refers to solvent peaks (DMSO-$d_6$, $D_2O$ and traces of water, ethanol and dichloromethane), according to one embodiment.

FIG. 8C shows GPC chromatograms of Polymer 1 prior to the addition of $H_2O_2$ (black line) and after degradation in 20% PBS/DMF solutions containing 100 μM, 1 mM, 50 mM and 100 mM $H_2O_2$ incubated at 37° C. for one day, according to one embodiment.

FIG. 9A and FIG. 9B show $^1H$ NMR spectra of Polymer 2 in DMSO-$d_6$, deuterium PBS (9A) without $H_2O_2$ and (9B) incubated with 50 mM $H_2O_2$ after 3 days at 37° C., where "s"

refers to solvent peaks (DMSO-$d_6$, $D_2O$ and traces of water, ethanol and dichloromethane), according to one embodiment.

FIG. 9C shows GPC chromatograms of Polymer 2 prior to the addition of $H_2O_2$ (black line) and after degradation in 20% PBS/DMF solutions containing 100 μM, 1 mM, 50 mM and 100 mM $H_2O_2$ incubated at 37° C. for one day, according to one embodiment.

FIG. 10 is a diagrammatic view of the $H_2O_2$-triggered release system, according to one embodiment.

FIGS. 11A to 11C illustrate TEM images of Polymer 1 nanoparticles in the absence of $H_2O_2$, incubated at 37° C. for 10 minutes, according to one embodiment.

FIGS. 12A to 12C illustrate TEM images of Polymer 1 nanoparticles in the absence of $H_2O_2$, incubated at 37° C. for 72 hours, according to one embodiment.

FIGS. 13A to 13D illustrate TEM images of Polymer 1 nanoparticles in the presence of 1 mM $H_2O_2$, incubated at 37° C. for 72 hours, according to one embodiment.

FIGS. 14A to 14D illustrate TEM images of Polymer 1 nanoparticles in the presence of 250 mM $H_2O_2$, incubated at 37° C. for 10 minutes, according to one embodiment.

Figures 15A, 15B:
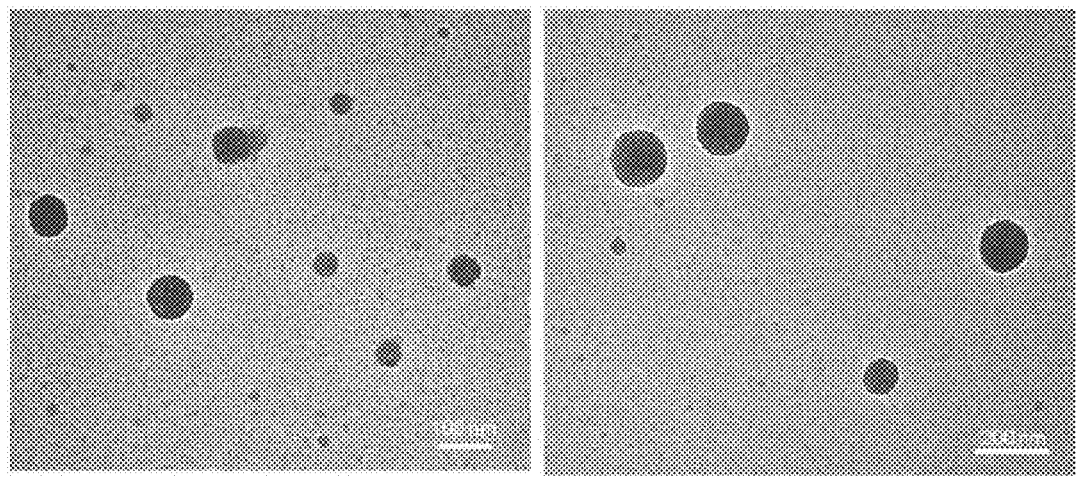

FIG. 15A and FIG. 15B illustrate TEM images of Polymer 2 nanoparticles incubated at 37° C. for 72 hours in the absence of $H_2O_2$, according to one embodiment.

Figure 16A:
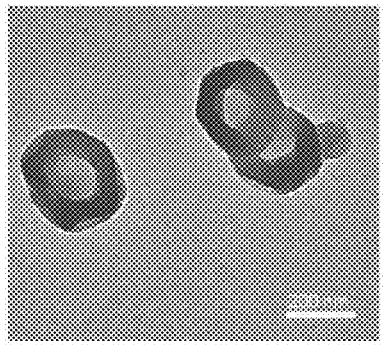
Figure 16B:
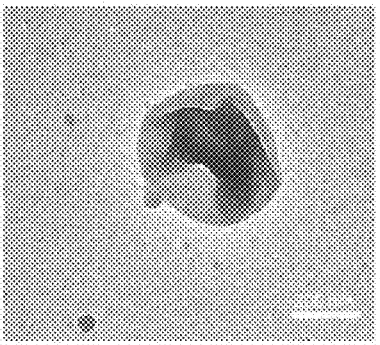
Figure 16C:
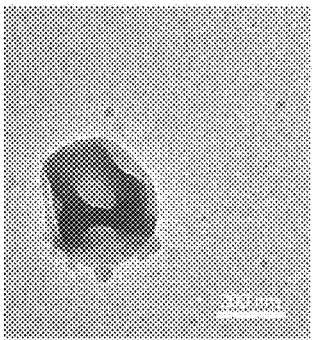

FIGS. 16A to 16C illustrate TEM images of Polymer 2 nanoparticles in the presence of 1 mM $H_2O_2$, incubated at 37° C. for 72 hours, according to one embodiment.

Figure 17A:
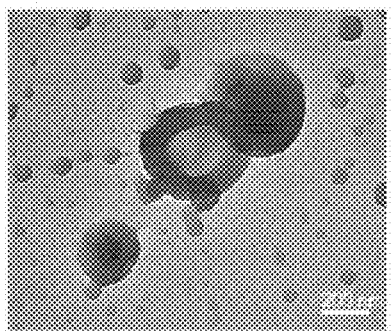
Figure 17B:
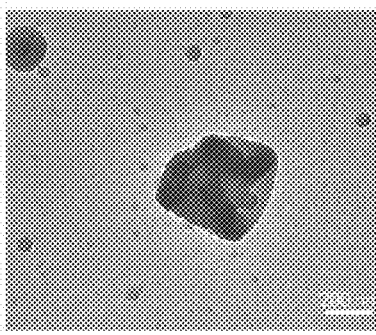
Figure 17C:
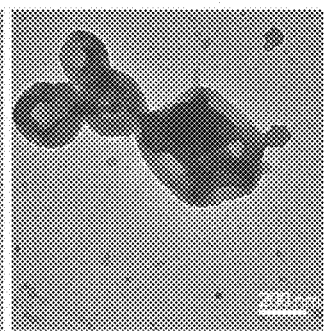

FIGS. 17A to 17C illustrate TEM images of Polymer 2 nanoparticles in the presence of 100 mM $H_2O_2$, incubated at 37° C. for 3 minutes, according to one embodiment.

Figure 18A:
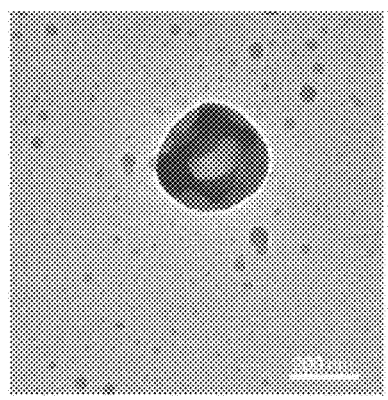
Figure 18B:
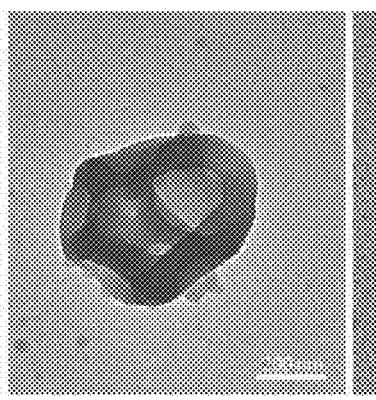
Figure 18C:
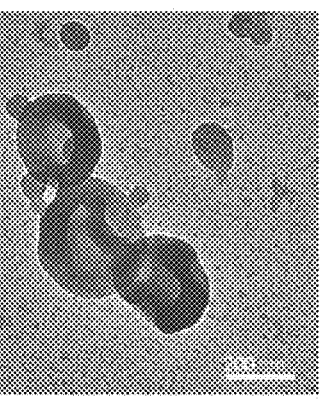

FIGS. 18A to 18C illustrate TEM images of Polymer 2 nanoparticles in the presence of 250 mM $H_2O_2$, incubated at 37° C. for 10 minutes, according to one embodiment.

FIGS. 19A to 19C illustrate TEM images of Polymer 2 nanoparticles in the presence of 100 μM $H_2O_2$, incubated at 37° C. for 72 hours, according to one embodiment.

FIGS. 20A to 20C illustrate TEM images of Polymer 2 nanoparticles in the presence of 50 μM $H_2O_2$, incubated at 37° C. for 72 hours, according to one embodiment.

Figure 21A:
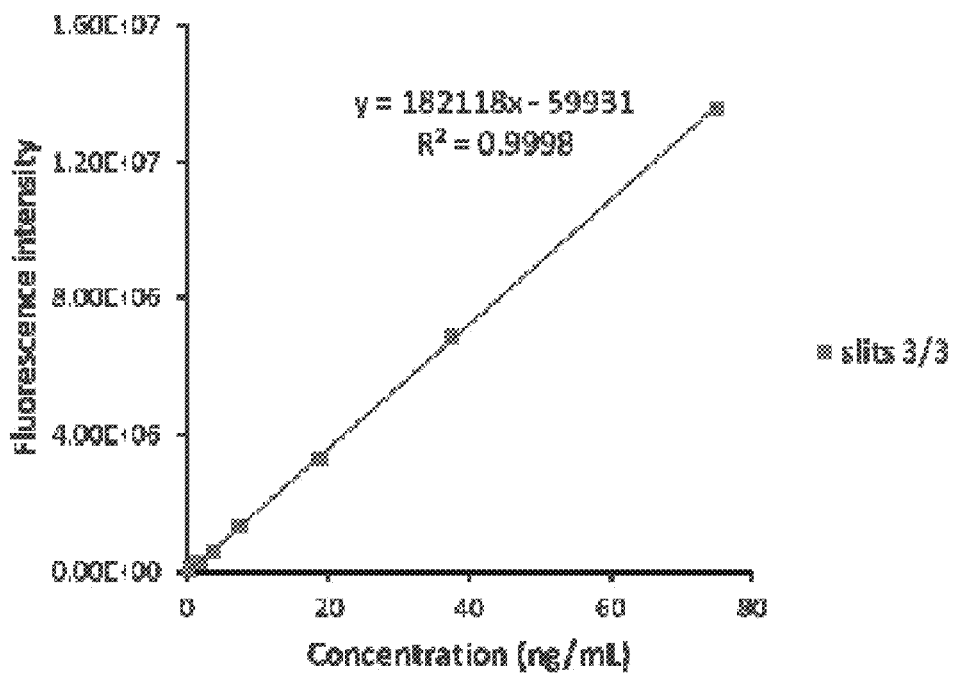
Figure 21B:
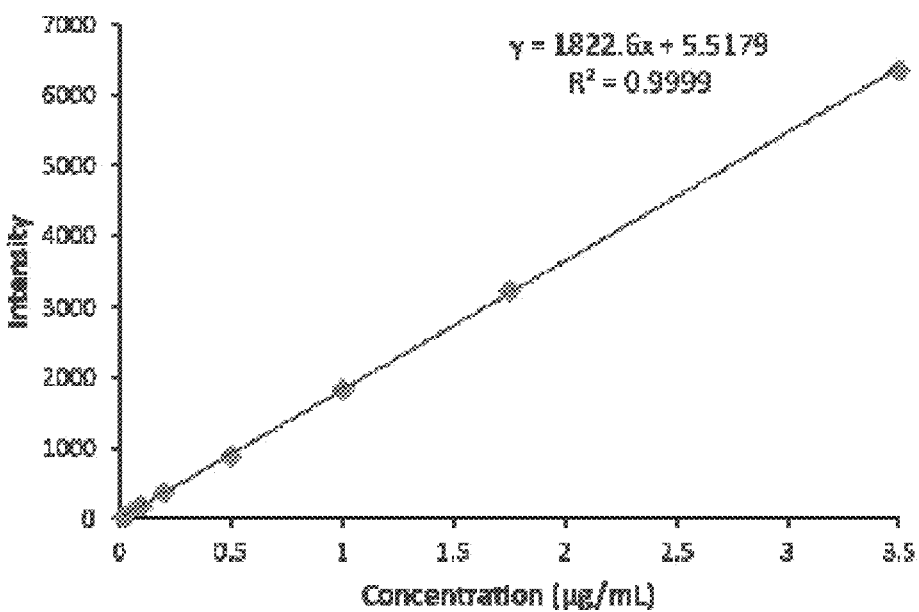

FIGS. 21A and 21B illustrate the calibration curves used for the determination of Nile red encapsulation efficiency (EE). Specifically, FIG. 21A illustrates the Nile red fluorescence intensity in acetone and FIG. 21B illustrates the HPLC detection.

Figure 22:
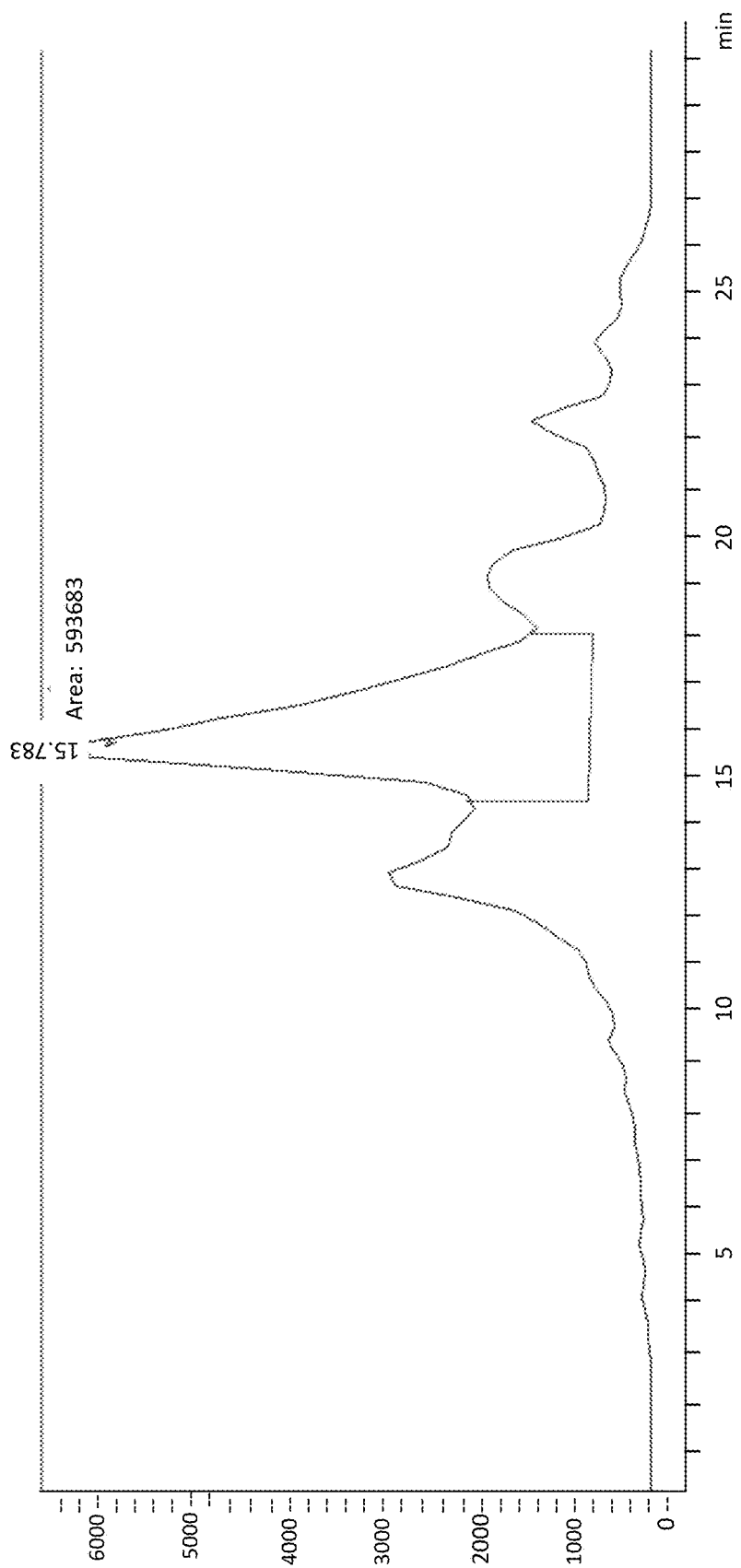

FIG. 22 is a representative LC-MS traces (mass detection of paclitaxel M+NA=876.0) after incubation in $H_2O_2$ (50 nM) for 4 days, according to one embodiment.

Figure 23:
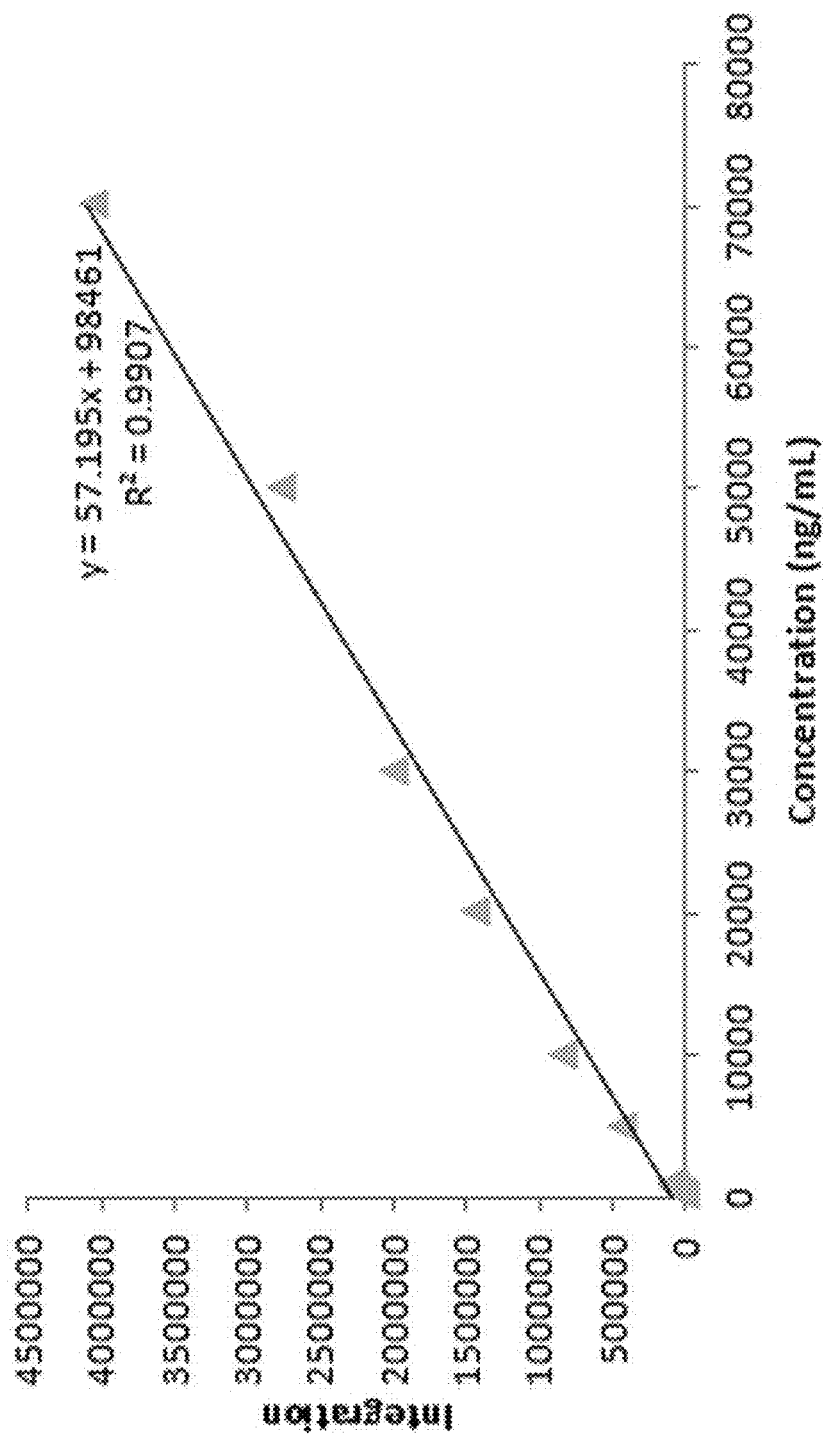

FIG. 23 is an exemplary calibration curve (peak area of paclitaxel), according to one embodiment.

Figure 24:
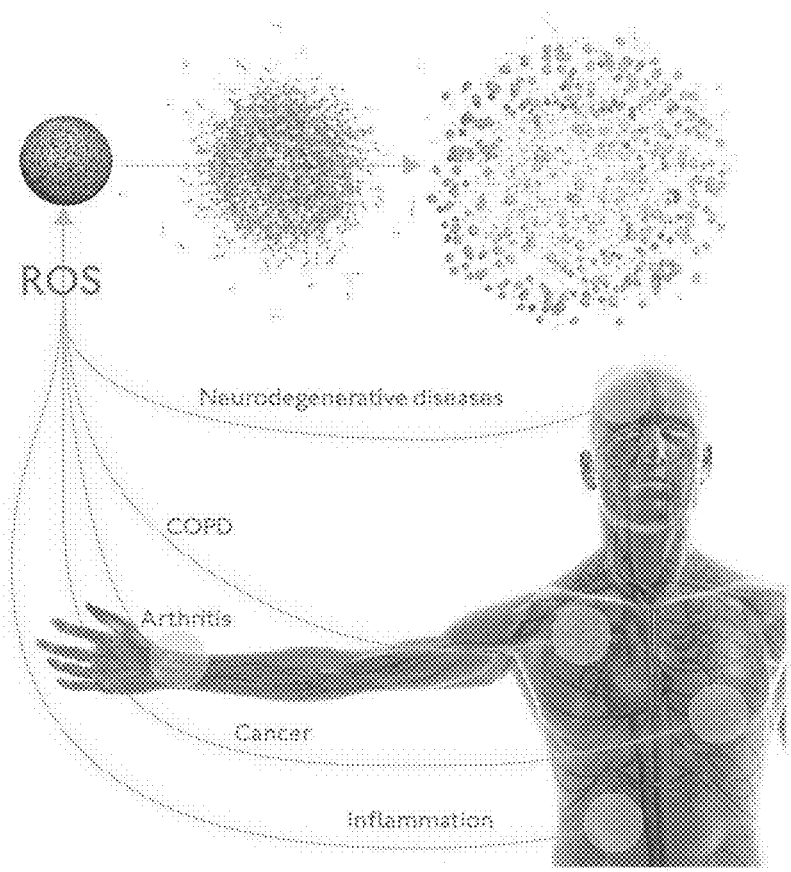

FIG. 24 provides an illustration of the major categories of disease involving high levels of ROS.

Figure 25:
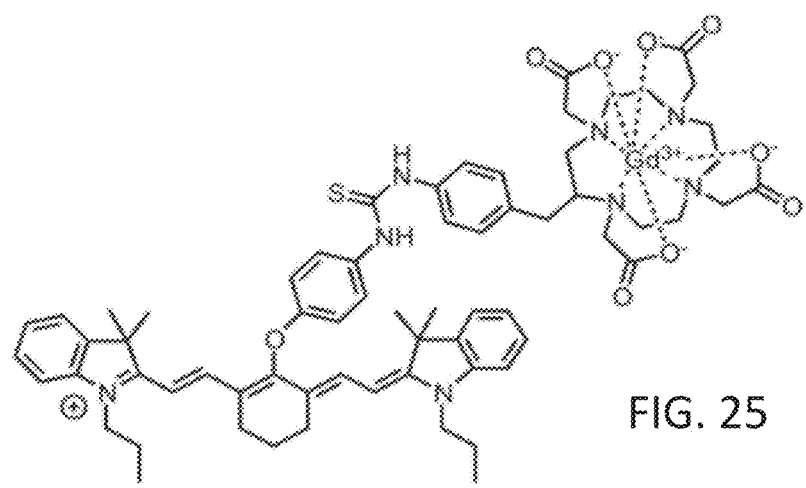

FIG. 25 illustrates the chemical structure of the magneto-luminescent contrast agent, IR780-DOTA.

Figure 26A:
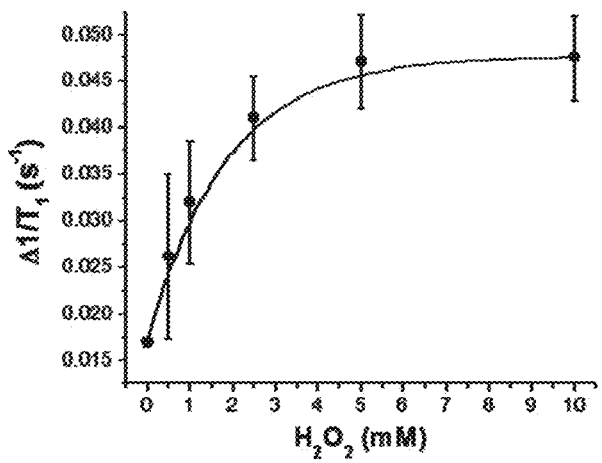
Figure 26B:
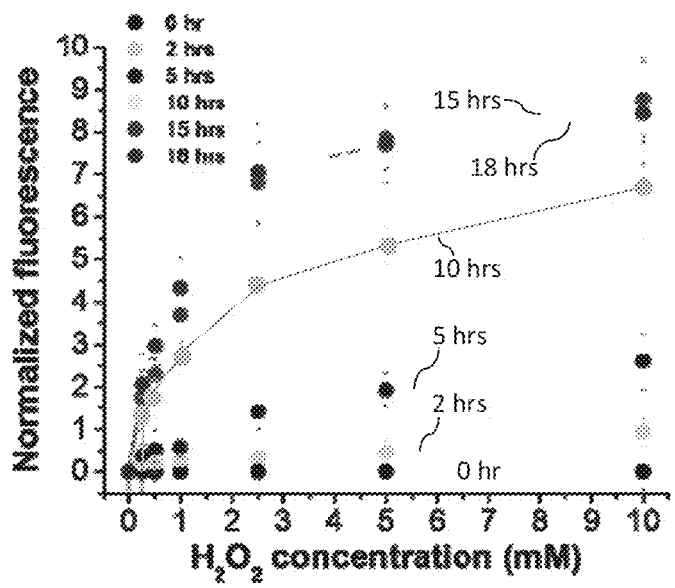
Figure 26C:
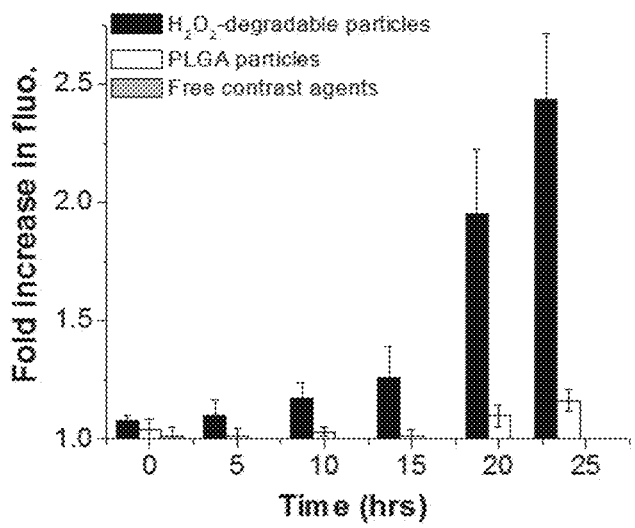

FIG. 26A to FIG. 26C illustrates that increasing concentrations of $H_2O_2$ triggers increases in $T_1$ relaxation rates (FIG. 26A) and fluorescence of the magneto-luminescent molecules encapsulated in the $H_2O_2$-responsive system (FIG. 26B). FIG. 26C illustrates that phorbol 12-myristate 13-acetate-activated dMPRO cells also activate fluorescence in the $H_2O_2$-responsive system.

Figure 27:
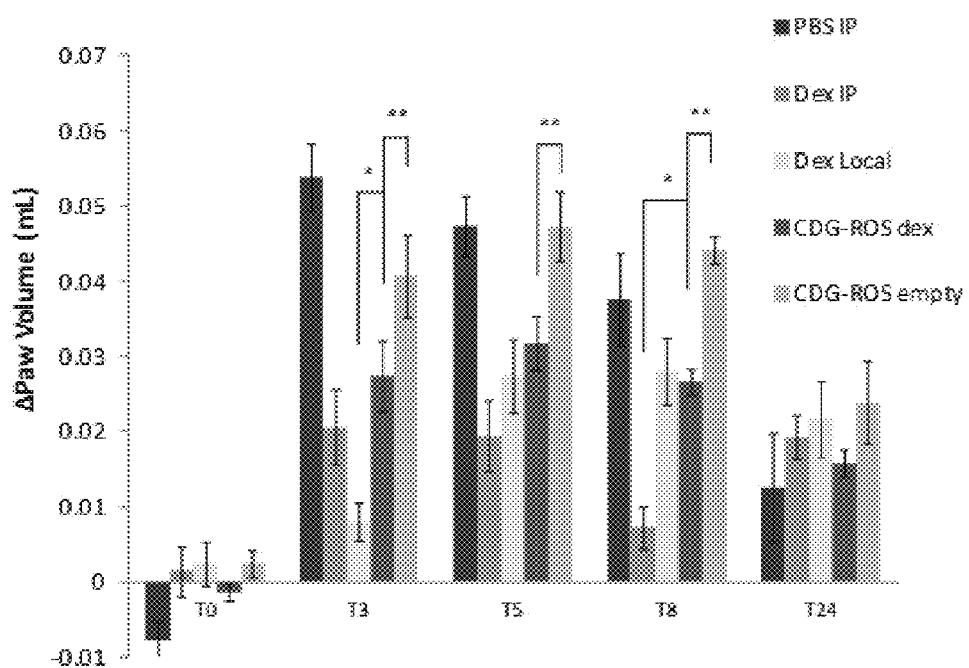

FIG. 27 illustrates that dexamethasone delivered locally in $H_2O_2$-responsive polymer (CDG-ROS) nanoparticles reduces carrageenan-induced paw swelling. Dex, dexamethasone. Paw volume difference is relative to contralateral paw injected with PBS instead of carrageenan.

Figures 28A, 28B:
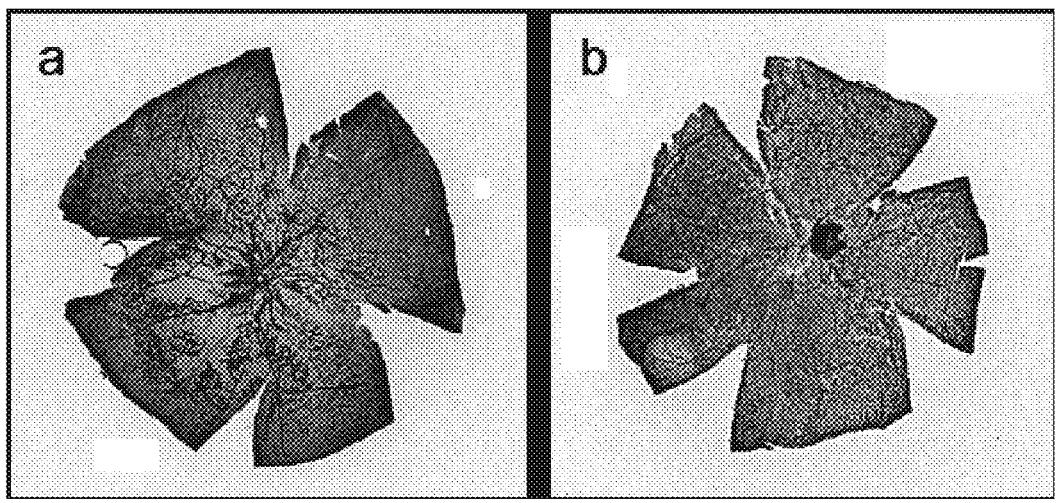

FIG. 28A and FIG. 28B illustrate that the VEGF-Trap retains therapeutic efficacy after formulation into polymeric nanoparticles. Isolectin IB4-stained flat-mount retinas from 17-day old mice exposed to 75% $O_2$ from day 7 to day 12. FIG. 28A illustrates that retinas of eyes injected at day 12 with PBS; and FIG. 28B illustrates VEGF-Trap-encapsulating $H_2O_2$-degradable nanoparticles. Representative of four replicates.

DETAILED DESCRIPTION OF ILLUSTRATIVE EMBODIMENTS

After reading this description it will become apparent to one skilled in the art how to implement the compositions and methods of the present disclosure in various alternative embodiments and alternative applications. However, although various embodiments of the present disclosure will be described herein, it is understood that these embodiments are presented by way of example only, and not limiting. As such, this detailed description of various alternative embodiments should not be construed to limit the scope or breadth of the present disclosure as set forth in the appended claims.

Cells obtain energy from the oxidation of a variety of organic molecules, and oxygen is the primary oxidant in the biochemical reactions that perform this function. Oxidative stress represents an imbalance between the production and manifestation of reactive oxygen species and a biological system's ability to readily detoxify the reactive intermediates or to repair the resulting damage.

In humans, oxidative stress contributes to diseases ranging from Alzheimer's, heart disease and stroke to macular degeneration, glaucoma and cancer. However, increased oxidative stress also causes an adaptive reaction which produces increased stress resistance and a long-term reduction of oxidative stress (called mitohormesis). Mitohormesis is associated with the anti-aging effects of glucose restriction and physical exercise.

The biocompatible polymeric materials described herein are capable of undergoing backbone degradation and thus release upon exposure to hydrogen peroxide thereby allowing for targeted drug delivery to diseased tissue.

EXEMPLARY TERMS

As used herein, the terms "comprising," "including," and "such as" are used in their open, non-limiting sense.

The term "about" is used synonymously with the term "approximately." Illustratively, the use of the term "about" indicates that values slightly outside the cited values, i.e., plus or minus 0.1% to 10%, which are also effective and safe.

"Antioxidants" include, e.g., butylated hydroxytoluene (BHT), butylated hydroxy-anisole (BHA), sodium ascorbate, and tocopherol.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone®, CL, Kollidon® CL, Polyplasdone® XL-10), larch arabogalactan, Veegum®, polyethylene glycol, waxes, sodium alginate, and the like.

"Pharmaceutically-acceptable excipients" include any commonly used materials in pharmaceutics and should be selected on the basis of compatibility with the active ingredient and the release profile properties of the desired dosage form. Exemplary pharmaceutically-acceptable excipients include, e.g., carriers, binders, suspending agents, disintegration agents, filling agents, surfactants, solubilizers, stabilizers, lubricants, wetting agents, diluents, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott William & Wilkins 1999).

"Oxidative stress" refers to the condition characterized by an excess of oxidants and/or a decrease in antioxidant levels. Cellular oxidants include, but are not limited to, one or more of: radicals of oxygen (superoxide anion, hydroxyl radical, and/or peroxy radicals); reactive non-radical oxygen species such as, for example, hydrogen peroxide and singlet oxygen; carbon radicals; nitrogen radicals; and sulfur radicals. The condition of oxidative stress results in, for example, cellular damage, inflammation, impaired performance of cells and/or cell death.

"Prevent" or "prevention" means no disorder or disease development if none had occurred, or no further disorder or disease development if there had already been development. Also considered is the ability of one to prevent or reduce some or all of the symptoms associated with the disorder or disease.

"Surfactants" include compounds such as sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF); and the like.

A "therapeutically effective amount" or "effective amount" is that amount of a compound, material, composition, and/or dosage form as described herein that is in at least some cases effective to achieve a particular biological result. Such results in at least some cases include, but are not limited to, reduction and/or prevention of oxidative stress. Such effective activity is achieved in at least some cases, for example, by causing the ingestion of compositions according to aspects of the present disclosure. The term "therapeutically effective amount" includes, for example, a prophylactically effective amount. An "effective amount" is an amount effective to achieve a desired pharmacologic effect or therapeutic improvement without undue adverse side effects. The effective amount of a pharmaceutical agent will be selected by those skilled in the art depending on the particular patient and the disease level. It is understood that "an effective amount" or "a therapeutically effective amount" varies in at least some cases from subject to subject, due to variation in metabolism of therapeutic agents, age, weight, general condition of the subject, the condition being treated, the severity of the condition being treated, and the judgment of the prescribing physician.

"Treat" or "treatment" includes preventing a disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression (or partial regression) of the disorder or disease, relieving a condition caused by the disease or disorder, stopping the symptoms of the disease or disorder, or reversing or partially reversing certain diseases and/or conditions. Thus, as used herein, the term "treat" is used synonymously with the term "prevent."

Oxidative Stress Cycle

Oxidative stress processes often have a self-regenerating nature. For example, oxidative stress leads to further oxidative stress and the cycle reinforces itself. By way of example only, moderate $H_2O_2$ or $OH^-$ disrupts the mitochondria of cells causing an increase of superoxide anion production. Disruption of mitochondria leads to increased hydrogen peroxide production and the effect becomes exponentially self-regenerating. This often results in a severe disorder. Disruption of an oxidative stress cycle allows natural mechanisms to address the source of the initial oxidative stress.

In certain instances, increased or undesired peroxide levels in a tissue (for example, ocular tissue) results from the inactivation (in a reversible reaction) of endogenous catalase by nitric oxide. Catalase activity is affected by the presence of nitric oxide which binds to the active center of catalase. When the nitric oxide molecule is present the catalase is unable to attach itself to a peroxide molecule. As the partial pressure of nitric oxide gas in the tissue drops, the nitric oxide dissociates from the catalase and the catalase becomes active again. Thus nitric oxide is a reversible inhibitor of catalase.

Inactivation of catalase results in the build-up of peroxide which results in damage to a tissue and an inflammatory response. As the inflammatory response increases, more nitric oxide is produced rendering more catalase inactive and increasing the concentration of peroxide. Because nitric oxide prevents the catalase from working, adding additional catalase often does not fully inhibit or sufficiently reduce peroxide build-up.

There are a number of agents that inactivate catalase, and result in the build-up of the oxidative cycle and cell death. For example, many chemotherapeutic agents are designed to activate or increase the oxidative cycle. Calcitriol, a catalase inhibitor, is used to kill cancer cells by peroxide build up.

As described herein, two polymeric structures were developed differing with respect to the linkage between the boronic ester group and the polymeric backbone. Both polymers are stable in aqueous solution at normal pH, and exposure to peroxide induces the removal of the boronic ester protecting groups at physiological pH and temperature, revealing phenols along the backbone, which undergo quinone methide rearrangement to lead to polymer degradation.

Faster backbone degradation was observed by NMR and GPC for Polymer 2 as compared to Polymer 1. Nanoparticles were formulated from these novel materials to analyze their oxidation triggered release properties. While nanoparticles formulated from Polymer 1 only released 50% of the reporter dye after exposure to 1 mM $H_2O_2$ for 26 h, nanoparticles formulated from Polymer 2 did so within 10 h and were able to release their cargo selectively in biologically relevant concentrations of $H_2O_2$.

Nanoparticles formulated from Polymer 2 showed a two-fold enhancement of release upon incubation with activated neutrophils while controls showed non-specific response to ROS producing cells. These polymers represent a novel, biologically relevant and biocompatible approach to biodegradable $H_2O_2$-triggered release systems that can degrade into small molecules, release their cargo, and should be easily cleared by the body.

The present invention provides a complementary polymeric system specifically sensitive to biologically relevant concentrations of $H_2O_2$, where aryl boronic ester protecting groups are introduced into each motif of the polymeric nanoparticle design. See, Fomina, N., et al, A. J. Am. Chem. Soc. 2010, 132, 9540. Without being bound by theory, this results in an amplification of the $H_2O_2$ sensitivity because each cleavage of the boronic ester leads to polymer backbone degradation.

Short polymeric strands (Polymer 1) and high molecular weight polymer (Polymer 2) are formulated into particles and such degradation of the polymer backbone is likely responsible for this systems high sensitivity to $H_2O_2$. Furthermore, the degradation products are smaller molecular weight species that are predicted to be more easily cleared by the body than larger polymer molecules. Moreover, the kinetics of degradation can be modulated using two linkage strategies between the peroxide activated triggering group and the backbone.

A recent study has shown that an ether linkage strategy provides both high hydrolytic stability and cleavage kinetics, though it has been only sparsely utilized. See, e.g., Jourden, J. L. M., et al., Chem. Commun. (Cambridge, U. K.) 2011, 47, 7968. This chemistry has been used most notably for the synthesis of ROS sensitive prodrugs to inhibit matrix metalloproteinase, an enzyme which is secreted as a ROS sensitive zymogen, and implicated in the reperfusion injury associated with stroke.

Exemplary Pharmaceutical Compositions

The compositions described herein are administered and dosed in accordance with good medical practice, taking into account the clinical condition of the individual patient, the site and method of administration, scheduling of administration, and other factors known to medical practitioners. In human therapy, it is important in many cases to provide a dosage form that delivers the required therapeutic amount of the drug in vivo, and renders the drug bioavailable in a timely manner.

Treatment dosages generally are titrated to optimize safety and efficacy. Typically, dosage-effect relationships from in vitro and/or in vivo tests initially provide useful guidance on the proper doses for subject administration. Studies in animal models generally are used for guidance regarding effective dosages for treatment of the conditions, disorders or diseases in accordance with the present disclosure. In terms of treatment protocols, it should be appreciated that the dosage to be administered will depend on several factors, including the particular agent that is administered, the route chosen for administration, the age of the subject, and the condition of the particular subject.

Generally speaking, one will desire a pharmaceutical composition that provides an amount of the active ingredient that is effective to achieve the therapeutic effect desired when administered to a subject. Determination of these parameters is well within the skill of the art. These considerations are well known in the art and are described in standard textbooks.

Topical Formulations

In some embodiments of the disclosure described herein, the pharmaceutical composition is a topical formulation comprising the $H_2O_2$ polymers described herein, at least one active ingredient and at least one pharmaceutically-acceptable excipient. Non-limiting examples of pharmaceutically-acceptable excipients useful in the topical formulations disclosed herein are: thickeners, including gums, celluloses, acrylic acids, colloidal solids, hydrogels, and thermoreversible polymers; oil phases; surfactants, including non-ionic, anionic, and cationic; solvents, including polar and non-polar; preservatives, including antimicrobial and chelating agents; and pH adjustors, such as diethanolamine, lactic acid, monoethanolamine, triethanolamine, sodium hydroxide and sodium phosphate.

In various embodiments, the topical formulation is formulated for direct application to a body surface including but not limited to the skin or mucous membranes such as the vagina, anus, throat, eyes and ears. In some embodiments, the topical formulation is epicutaneous, i.e. directly applied to the skin. In various embodiments, the topical formulation is in the form of a cream, ointment, shake lotion, gel, powder, solid, transdermal patch, tincture, paste, vapor, tape, sponge or lotion.

Intravenous Formulations

In some embodiments of the disclosure described herein, the pharmaceutical composition is an intravenous formulation comprising the $H_2O_2$ polymers described herein, at least one active ingredient and at least one pharmaceutically-acceptable excipient. Non-limiting examples of pharmaceutically-acceptable excipients useful in the intravenous formulations disclosed herein are surfactants, including non-ionic, anionic, and cationic; solvents, including polar and non-polar; preservatives, including antimicrobial, antioxidants and chelating agents; and pH adjustors, such as diethanolamine, lactic acid, monoethanolamine, triethanolamine, sodium hydroxide and sodium phosphate.

Sustained Release Formulations

In some embodiments of the disclosure described herein, the pharmaceutical composition is a sustained release formulation comprising the $H_2O_2$ polymers described herein, at least one active ingredient and at least one pharmaceutically-acceptable excipient. Non-limiting examples of pharmaceutically-acceptable excipients useful in the sustained release formulations disclosed herein are: thickeners, including gums, celluloses, acrylic acids, colloidal solids, hydrogels, and thermoreversible polymers; oil phases; surfactants, including non-ionic, anionic, and cationic; solvents, including polar and non-polar; preservatives, including antimicrobial, antioxidants and chelating agents; and pH adjustors, such as diethanolamine, lactic acid, monoethanolamine, triethanolamine, sodium hydroxide and sodium phosphate.

In various embodiments, the sustained release formulation is an ophthalmic formulation, a parenteral formulation, a pellet formulation, or a transdermal formulation.

In some embodiments, the sustained release ophthalmic formulation comprises a water-based gel, a suspension, an ointment, an ocular insert, or small colloidal carrier particles (such as liposomes, microspheres, microcapsules, nanoparticles, or nanocapsules). In some embodiments, the sustained release parenteral formulation comprises an oily vehicle, aqueous suspension, emulsion, microsphere, or an implantable drug delivery system.

Implants

In some embodiments of the disclosure described herein, the pharmaceutical composition is delivered through an implant comprising the $H_2O_2$ polymers described herein, at least one active ingredient and at least one pharmaceutically-acceptable excipient. In various embodiments, the implant is composed of a number of capsules. In some embodiments the implant is biodegradable.

Exemplary Methods of Treatment

Disclosed herein, in certain embodiments, are methods of reducing or preventing oxidative stress processes in an individual in need thereof, comprising administering to the individual a composition comprising the $H_2O_2$ polymers described herein and at least one active ingredient.

Skin Indications

In aspects of the disclosure, the methods and compositions described herein may be useful in reversing, treating or preventing skin conditions or disorders including but not limited premature aging, burns, Dermatitis; Psoriasis; Vitiligo, Androgenic Alopecia (loss of hair) and Onset of Gray Hair.

Eye Indications

As discussed above, increased or undesired peroxide levels in a tissue (for example, ocular tissue) results from the inactivation (in a reversible reaction) of endogenous catalase by nitric oxide. The inactivation of catalase is associated with the destruction of nerve cells (glaucoma), retinal macular cells (AMD), lacrimal and epithelial cells (dry eye) and lens cells (cataract).

Non-limiting examples of diseases and disorders for which the compositions described herein are useful include Macular Degeneration (including but not limited to neovascular age-related macular degeneration); Cataract Formation; Keratoconusl; Cystoid Macular Edema; dry eye syndrome; Glaucoma; Reduction of Inflammation; Dry Eyes; Degenerative Retinal Damage (ARMD); Cataractogenesis; Retinopathy of Prematurity (ROP); Ocular Uveitis; and Senile Cataracts.

Joint Indications

In aspects of the disclosure, the methods and compositions described herein may be useful in reversing, treating or preventing joint conditions/diseases associated with oxidative stress. These conditions include, but are not limited to, Inflammation; Rheumatoid Arthritis; and Osteoarthritis.

Wound Healing Indications

In aspects of the disclosure, the methods and compositions described herein are useful in reversing, treating or preventing ocular wounds associated with oxidative stress. These conditions include, but are not limited to, pterygium, glaucoma, refractive corneal surgery such as PRK, LASIK, Intacs, lamellar corneal procedures, CK, and other thermokeratoplasty treatments and lens based refractive surgery, scleral surgery, retinal surgery or retinal or glaucoma laser surgery and intraocular such as cataract and eye lid surgery.

Heart Indications

In aspects of the disclosure, the methods and compositions described herein are useful in reversing, treating or preventing heart conditions/diseases associated with oxidative stress. These conditions include, but are not limited to, Angioplasty; Keshan Disease (Selenium Deficiency); Myocardial Infarction; Atherosclerosis (ASVD) and Arterial Sclerosis.

Lung Indications

In aspects of the disclosure, the methods and compositions described herein are useful in reversing, treating or preventing lung conditions/diseases associated with oxidative stress. These conditions include, but are not limited to, Asthma; Acute Respiratory Distress Syndrome (ARDS); Hyperoxia and Pulmonary Edema.

Local or Systemic Indications

In aspects of the disclosure, the methods and compositions described herein are useful in reversing, treating or preventing local and systemic conditions/diseases associated with oxidative stress. These conditions include, but are not limited to, Inflammatory Bowel Disease (IBD); Crohn's Disease; Ischemic Bowel Disease; Cancer; Inflammatory Immune Response; Diabetes; Injury Ischemia Reflow Injury; Vasospasm; Hemolytic Anemia; Progeria and Progressive Systemic Sclerosis.

Kidney & Liver Indications

In aspects of the disclosure, the methods and compositions described herein are useful in reversing, treating or preventing kidney and liver conditions/diseases associated with oxidative stress. These conditions include, but are not limited to, Hepatic Cirrhosis; Renal Graft; Glomerulonephritis and Endotoxin Liver Injury.

Neurological Indications

In aspects of the disclosure, the methods and compositions described herein are useful in reversing, treating or preventing neurological conditions/diseases associated with oxidative stress. These conditions include, but are not limited to, Parkinson's Disease; Alzheimer's Disease; Schizophrenia; Cerebral Edema; Cerebral Infarction (Stroke); Epilepsy; Bipolar Disorder; Trauma and Neurotoxins.

Aging-Related Indications

In aspects of the disclosure, the methods and compositions described herein are useful in reversing, treating or preventing diseases and symptoms associated with aging. These conditions include, but are not limited to, wrinkling, grey hair, baldness, presbyopia, cataracts, hearing loss, hypertension, and memory loss.

The above description of the disclosed embodiments is provided to enable any person skilled in the art to make or use the methods and compositions of the present disclosure. Various modifications to these embodiments will be readily apparent to those skilled in the art, and the generic principles described herein can be applied to other embodiments without departing from the spirit or scope of the disclosure. Thus, it is to be understood that the description and drawings presented herein represent a presently preferred embodiment of the disclosure and are therefore representative of the subject matter which is broadly contemplated by the present disclosure. It is further understood that the scope of the present disclosure fully encompasses other embodiments that may become obvious to those skilled in the art and that the scope of the present disclosure is accordingly not limited.

EXAMPLES

General Procedures and Instrumentation

Unless otherwise noted, all chemicals were obtained from commercial sources and used without further purification. All reactions were carried out under a nitrogen atmosphere in oven dried glassware unless otherwise noted. All organic solvents were removed under reduced pressure using a rotary evaporator.

Flash column chromatography purification was performed using a Teledyne Isco Combiflash Companion with RediSep Rf prepacked silica columns. Thin layer chromatography was performed with EMD TLC Silica gel 60 $F_{254}$ glass plates. Unless otherwise noted, $^1H$ NMR spectra were acquired using a Varian 400 MHz NMR spectrometer and $^{13}C$ NMR spectra were acquired using a Varian NMR spectrometer at 100 MHz. Chemical shifts are reported as δ in units of parts per million (ppm) relative to chloroform (δ 7.26, s) or methanol (δ 3.30, septet). Multiplicities are reported as follows: s (singlet), d (doublet), t (triplet), q (quartet), dd (doublet of doublets), m (multiplet), br (broadened), or app (apparent). Coupling constants are reported as a J value in Hertz (Hz).

The number of protons (n) for a given resonance is indicated as nH, and is based on spectral integration values. $^{13}C$ NMR spectra are reported as δ in units of parts per million (ppm) relative to chloroform-d (δ 77.16, t) or methanol-$d_4$ (δ 49.00, septet). Particle size and distribution (Z-average and PDI) measurements were determined using a Malvern Zetasizer Nano ZS dynamic light-scattering instrument.

Gel permeation chromatography was performed with a Waters e2695 instrument with a series of Styragel HR4 and Styragel HR2 columns in DMF with 0.01% LiBr at 37° C. The instrument was calibrated with monodisperse polystyrene standards. Fluorescence measurements were determined with a Horiba Jobin Yvon Fluorolog.

Statistics were performed using PASW Statistics 18 software. Significance was tested using one way ANOVA to compare multiple variables. Particles were imaged directly using a FEI XL30 Ultra High Resolution SEM. Paclitaxel release was measured with a LC-MS Agilent 160 Infinity (binary pump, UV-vis 1260 DAD, 6120 Quadrupole LC/MS ESI source) with a RP-18 column.

Example 1

Figure 1A:
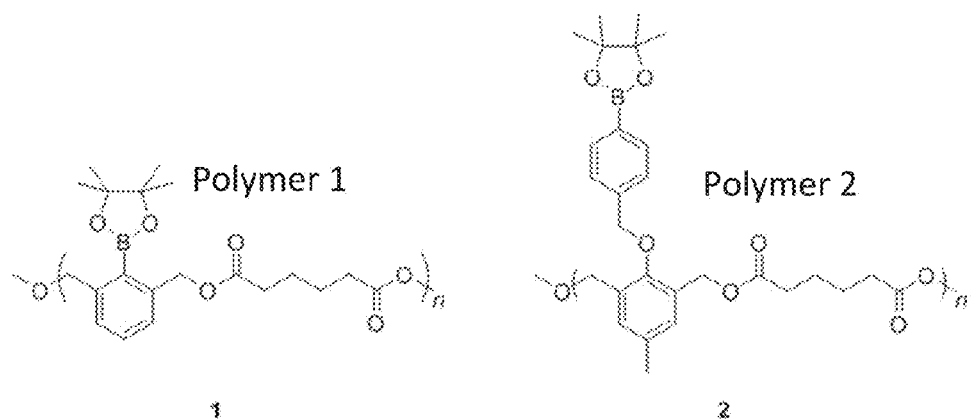
FIG. 1A shows the chemical structures of Polymer 1 and Polymer 2.
Figure 1B:
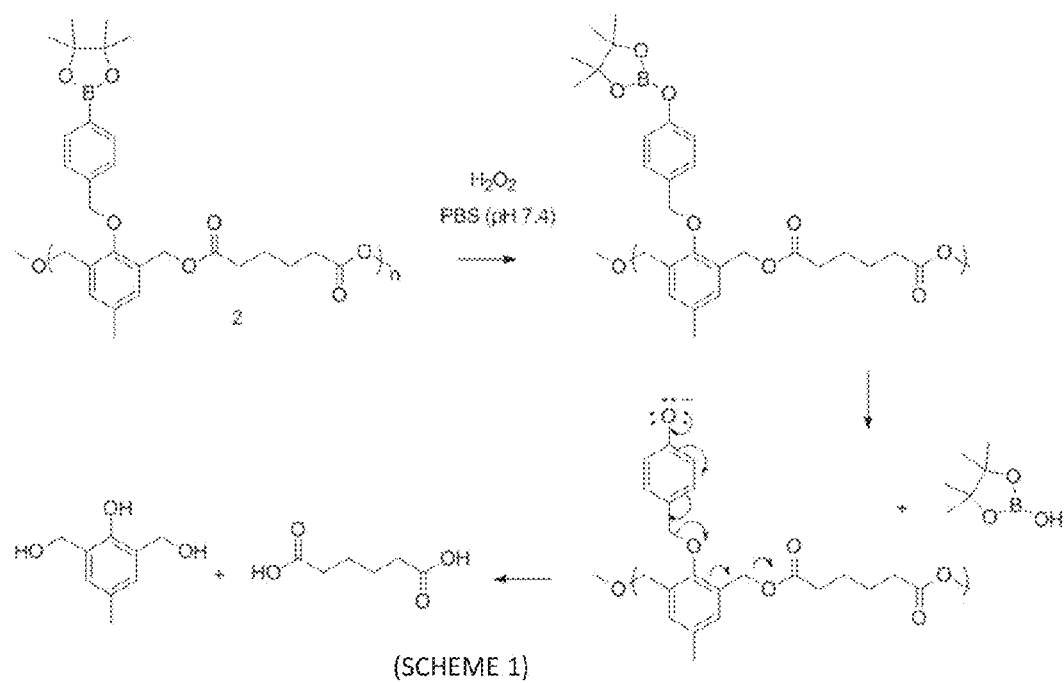
FIG. 1B illustrates Scheme 1, showing a mechanism of polymeric particle 2 degradation upon exposure to hydrogen peroxide ($H_2O_2$), according to one embodiment.
Figure 1C:
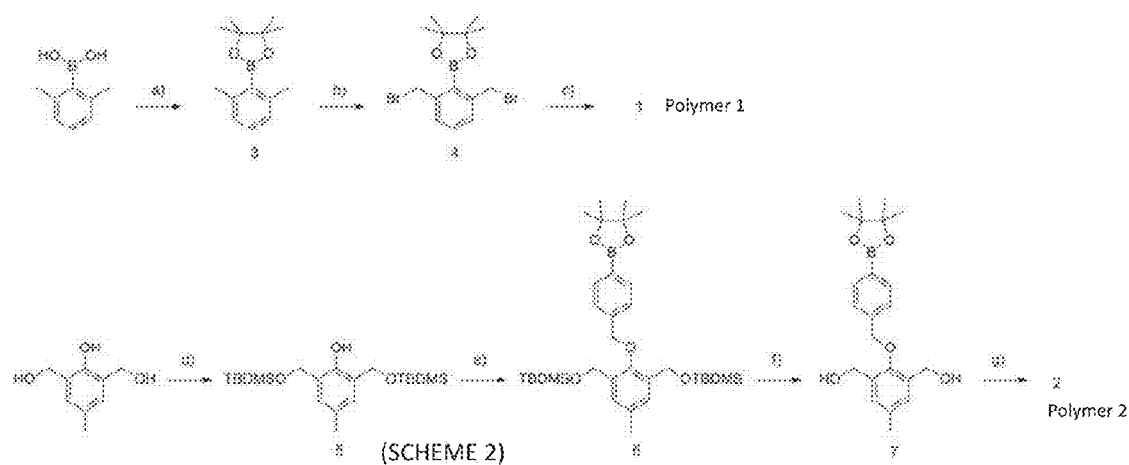
FIG. 1C illustrates Scheme 2, showing Synthesis of $H_2O_2$ degradable Polymer 1 and Polymer 2, according to one embodiment. (a) pinacol, $C_6H_6$ (84%), (b) AIBN, NBS, $CCl_4$ (55%), (c) adipic acid, $Bu_4NOH$, $CHCl_3$ (96%), (d) TBDM-SCl, imidazole, DMF (95%), (e) 4-Bromomethylphenyl boronic acid pinacol ester, $K_2CO_3$, DMF (79%), (f) pTsOH, MeOH (90%), (g) adipoyl chloride, pyridine, DCM (82%).

Synthesis of Compound 3, Scheme 2 (FIG. 1C)

2,6-dimethylphenylboronic acid (2.5 g, 16.67 mmol) and pinacol (2.36 g, 20.0 mmol) were added to a round bottom flask. The solids were dissolved in benzene (66.67 mL). A Dean-Stark apparatus/distilling receiver was attached to the flask and filled with benzene. A water cooled condenser was attached to the Dean-Stark apparatus. The reaction was heated to a vigorous reflux and stirred overnight.

Afterwards, the reaction was removed from heat allowed to cool to room temperature. Then, the solution was concentrated under reduced pressure, taken up in a minimal volume of benzene, and purified with a silica gel column using EtOAc/Hexanes. Concentration of selected fractions under reduced pressure afforded the product as a colorless oil (3.24 g, 84%).

$^1$H NMR (CDCl$_3$): δ 7.12 (t, J=8.0 Hz, 1H), 6.95 (d, J=8.0 Hz, 2H), 2.40 (s, 6H), 1.40 (s, 12H). $^{13}$C CDCl$_3$): δ 141.6, 129.1, 126.4, 83.4, 24.9, 22.1. ESI-MS (+): m/z calc. for C$_{14}$H$_{21}$BO$_2$: 232.16. found: 233.02 [M+H]$^+$. High resolution ESI-TOF MS, m/z (M$^+$) calcd. 233.1707. found 233.1712.

Example 2

Synthesis of Compound 4, Scheme 2 (FIG. 1C)

To a round bottom flask, boronic ester 3 (1.6 g, 6.9 mmol), AIBN (0.1, 0.7 mmol), and NBS (2.6 g, 14.4 mmol) were added. Carbon tetrachloride was added to the flask. The reaction was refluxed and stirred overnight. Afterwards, the suspension was filtered and the filtrate was concentrated under reduced pressure. The solid was dissolved in a mixture of CH$_2$Cl$_2$, acetone, and EtOAc.

The resulting solution was purified on silica gel using EtOAc/Hexanes. Selected fractions were concentrated to give a white solid (2.36 g, 88%). To achieve higher purity, the white solid was recrystallized in a minimal volume of hot i-PrOH or in a mixture of hexane and ethylacetate (1.48 g, 55%).

$^1$H NMR (CDCl$_3$): δ 7.29 (m, 3H), 4.82 (s, 4H), 1.47 (s, 12H). $^{13}$C CDCl$_3$): δ 144.3, 130.6, 130.0, 84.4, 34.1, 25.3. ESI-MS (+): m/z calc. for C$_{14}$H$_{19}$BBr$_2$O$_2$: 387.98. found: 407.96 [M+NH$_4$]$^+$, 412.94 [M+Na]$^+$. High resolution ESI-TOF MS, m/z (M$^+$) calcd. 408.0163. found 408.0166.

Example 3

Synthesis of Polymer 1, Scheme 2 (FIG. 1C)

Tetrabutylammonium hydroxide, 40% in H$_2$O, (2.9 mL) was added to a reaction vessel containing adipic acid (238.2 mg, 1.6 mmol). The solution was heated to 62° C. till a homogeneous solution was formed. A chloroform (6.2 mL) solution of benzyl bromide 3 (952.8 mg, 2.4 mmol) was added. The reaction was heated at 62° C. overnight.

The solution was then partitioned between H$_2$O and CH$_2$Cl$_2$ and extracted with 2 portions of CH$_2$Cl$_2$. The organic layers were combined and washed with brine, dried over Na$_2$SO$_4$, and filtered. The filtrate was concentrated. The solid was taken up in methanol and partitioned with H$_2$O. The solution was extracted with 2 portions of EtOAc. The combined organic layers were washed with brine, dried over Na$_2$SO$_4$, filtered, and concentrated.

The obtained white solid (770 mg) was purified by gel filtration using Sephadex G10 in DMF. This allowed the separation of the target polymer from salts, smallest oligomers, unreacted and excess of monomers (589 mg, 96%).

(M$_w$=10623, PDI=1.9, determined by gel-permeation chromatography (GPC) relative to polystyrene standards). $^1$H NMR (DMSO-d$_6$, PBS-D$_2$O): δ 7.27-7.37 (m, 3H), 5.03 (br s, 4H), 2.28 (br s, 4H), 1.44 (br s, 4H), 1.13-1.30 (m, 12H). $^{13}$C CDCl$_3$): δ 172.3, 140.6, 138.4, 129.9, 128.9, 127.4, 83.8, 79.4, 73.7, 65.9, 65.7, 33.1, 25.2, 25.1, 24.6, 24.5, 23.9, 23.8, 20.1, 19.8.

Example 4

Alternative Synthesis of Polymer 1

To a round bottom flask, compound 4 (0.5 g, 1.3 mmol) and adipic acid (0.18 g, 1.3 mmol) were added. The solids were taken up in 4.4 mL of DMF and DBU (0.5 mL, 3.4 mmol) was added dropwise. The solution was heated to 70° C. and the homogeneous solution was stirred overnight.

The reaction was partitioned between CH$_2$Cl$_2$ and phosphate buffered saline (PBS) aqueous buffer. The organic layer was washed with 3 portions of PBS buffer and 1 portion of brine. The organic layer was dried over Na$_2$SO$_4$, filtered, and concentrated under vacuum; 0.45 g of crude yellow solid was isolated (93%).

Example 5

Synthesis of Compound 5, Scheme 2 (FIG. 1C)

2,6-bis-(hydroxymethyl)-p-cresol (10 g, 57.7 mmol) and imidazole (8.90 g, 130.7 mmol) were dissolved in 40 mL dry DMF and cooled to 0° C. TBDMSCl (19.72 g, 126.9 mmol) dissolved in 30 mL dry DMF was added dropwise. The reaction mixture was stirred for 2 h at room temperature and monitored by TLC (Hex/EtOAc 95:5).

After completion, the reaction mixture was diluted with Et2O, and was washed 3 times with water. The organic layer was separated, dried over Na$_2$SO$_4$ and evaporated under reduced pressure. The crude product was purified by flash-chromatography on silica gel (Hex/EtOAc 95:5) to give compound 5 (21.65 g, 95%) as a colorless oil.

$^1$H NMR (CDCl$_3$): δ 8.04 (s, 1H), 6.90 (s, 2H), 4.82 (s, 4H), 2.25 (s, 3H), 0.94 (s, 18H), 0.12 (s, 12H). $^{13}$C CDCl$_3$): δ 151.1, 128.4, 126.3, 125.9, 63.2, 26.0, 20.8, 18.4, −5.2. ESI-MS (+): m/z calc. for C$_{21}$H$_{40}$O$_3$Si$_2$: 396.25. found: 419.16 [M+Na]$^+$.

Example 6

Synthesis of Compound 6, Scheme 2 (FIG. 1C)

Compound 5 (939 mg, 2.36 mmol) was dissolved in 5 mL dry DMF and cooled to 0° C. K$_2$CO$_3$ (392 mg, 2.83 mmol) was added and the solution stirred at 0° C. for 10 min before the addition of 4-bromomethylphenyl boronic acid pinacol ester (738 mg, 2.36 mmol). The reaction mixture was stirred overnight at room temperature and monitored by TLC (Hex/EtOAc 85:15).

After completion, the reaction mixture was diluted with Et$_2$O, and was washed with a saturated solution of NH$_4$Cl, and then with brine. The organic layer was separated, dried over MgSO$_4$ and evaporated under reduced pressure. The crude product was purified by flash-chromatography on silica gel (Hex/EtOAc 95:5) to give compound 6 (1.14 g, 79%) as a colorless oil.

$^1$H NMR (CDCl$_3$): δ 7.83 (d, J=8.0 Hz, 2H), 7.42 (d, J=8.0 Hz, 2H), 7.17 (s, 2H), 4.88 (s, 2H), 4.70 (s, 4H), 2.34 (s, 3H), 1.36 (s, 12H), 0.91 (s, 18H), 0.06 (s, 12H). $^{13}$C CDCl$_3$): δ 151.1, 140.9, 135.1, 133.9, 133.8, 128.0, 127.1, 84.0, 76.2, 60.5, 26.1, 25.0, 21.3, 18.6, −5.1. ESI-MS (+): m/z calc. for C$_{34}$H$_{57}$BO$_5$Si$_2$: 612.38. found: 635.42 [M+Na]$^+$.

Example 7

Synthesis of Compound 7, Scheme 2 (FIG. 1C)

Compound 6 (195 mg, 0.32 mmol) was dissolved in 1 mL methanol. Catalytic amount of pTsOH (12.2 mg, 0.06 mmol) was added. The reaction mixture was stirred at room temperature for an hour and monitored by TLC (Hex/EtOAc 1:1). After completion of the conversion, the solvent was removed under reduced pressure. The crude was purified by flash-chromatography on silica gel (Hex/EtOAc 1:1) to give compound 6 (109.2 mg, 90%) as a white solid.

$^1$H NMR (CDCl$_3$): δ 7.85 (d, J=8.0 Hz, 2H), 7.44 (d, J=8.0 Hz, 2H), 7.16 (s, 2H), 4.97 (s, 2H), 4.67 (d, J=8.0 Hz, 4H), (2.33 (s, 3H), 1.36 (s, 12H). $^{13}$C CDCl$_3$): δ 152.7, 140.0, 135.3, 134.6, 134.0, 129.7, 127.3, 84.0, 77.0, 61.1, 25.0, 21.0. ESI-MS (+): m/z calc. for C$_{22}$H$_{29}$BO$_5$: 384.21. found: 402.19 [M+NH$_4$]$^+$, 407.21 [M+Na]$^+$.

Example 8

Synthesis of Polymer 2, Scheme 2 (FIG. 1C)

Monomer 7 (786.7 mg, 2.05 mmol) and distilled adipoyl chloride (374.7 mg, 2.05 mmol) were dissolved in 5 mL dry DCM. Anhydrous pyridine (971.6 mg, 12.28 mmol) was added dropwise and the reaction mixture was stirred at room temperature overnight.

Then, the crude mixture was concentrated under reduced pressure to 2 mL and precipitated into 40 mL cold ethanol. The crude polymer was further purified by repeated reprecipitations in cold ethanol (4×40 mL). This allowed the separation of the target polymer from smallest oligomers and pyridine. (yellow solid, 838.5 mg, 92%).

(M$_w$=51261, PDI=1.4, determined by gel-permeation chromatography (GPC) relative to polystyrene standards). $^1$H NMR (600 MHz, CDCl$_3$): δ 7.82 (d, J=6.0 Hz, 2H), 7.41 (d, J=12.0 Hz, 2H), 7.15 (s, 2H), 5.14 (s, 4H), 4.93 (s, 2H), 2.31 (s, 7H), 1.63 (s, 4H), 1.33 (s, 12H). $^1$H NMR (600 mHz, DMSO-d$_6$, PBS-D$_2$O): δ 8.50 (s, 2H), 7.79 (s, 2H), 7.39 (s, 2H), 4.12 (s, 6H), 3.41 (s, 6H), 1.47 (s, 1H), 1.12 (s, 1H), 1.02 (s, 12H). $^{13}$C (125 MHz, CDCl$_3$): δ 173.2, 153.9, 140.0, 135.2, 134.4, 131.5, 129.5, 126.9, 83.9, 77.2, 61.5, 34.0, 25.0, 24.4, 20.9.

Example 9

Design of H$_2$O$_2$-Sensitive Polymers

Polymer 1 and Polymer 2 (see FIG. 1A) differ in the linkage type between the pendant boronic ester protecting groups and the polymer backbone. Polymer 1 has a direct linkage between the polymer backbone and the protecting group, while Polymer 2 has a benzylic ether boronic ester pendant to the backbone.

Example 10

Mechanism of H$_2$O$_2$-Induced Polymer Degradation

Upon exposure to H$_2$O$_2$ the aryl boronic ester group is oxidized, and subsequently hydrolyzed to unmask a phenol. As illustrated in Scheme 1 (see FIG. 1B), this initiates a quinone methide rearrangement to degrade the polymer.

Example 11

Monomer and Polymer Synthesis

H$_2$O$_2$ sensitive nanoparticles were formulated from Polymer 1 and Polymer 2. Polymer 1 was synthesized according to Scheme 2 (see FIG. 1C), which began with the protection of 2,6-dimethylphenylboronic acid with pinacol which afforded good yields (84%) of boronic ester (compound 3).

Figure 2:
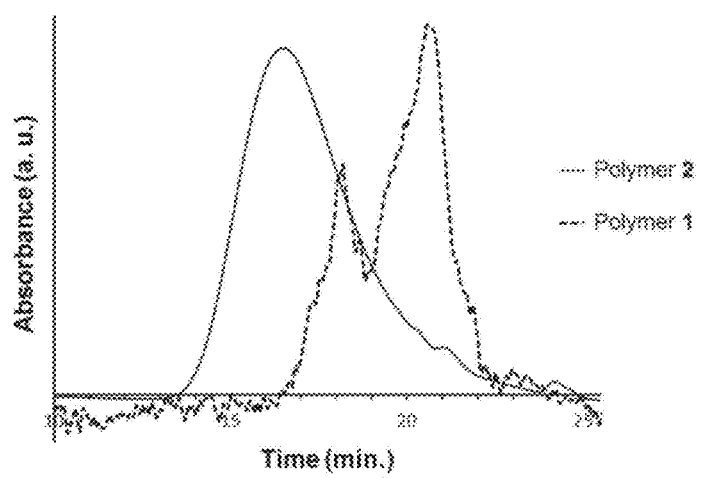
FIG. 2 is a plot showing GPC traces of Polymer 1 (Mw=10.6 kDa, PDI=1.9) and Polymer 2 (Mw=51.3 kDa, PDI=1.4), according to one embodiment.

Subsequent benzylic bromination with N-bromosuccinimide (NBS) and 2,2'-azobis(2-methylpropionitrile) (AIBN) gave the desired monomer (55% yield). The monomer was then combined with adipic acid in the presence of a phase transfer catalyst, Bu$_4$NOH, to give the H$_2$O$_2$ reactive polymer (PS standard: M$_w$=10623, PDI=1.9). As shown in FIG. 2 (dashed line), the GPC for this polymer is not smooth and has a high PDI. This is consistent with a step growth polymerization.

As this direct linkage polymer is synthetically challenging, only short polymeric strands were isolated. However, these led to the successful formulation of particles and encapsulation of Nile red within, thus the molecular weight was sufficient for controlled release. Other methods of polymerization were extensively investigated. Pyridine in dimethyl sulfoxide (DMSO) and dimethylformamide (DMF) failed to give high conversion to polymer. 1,8-diazabicyclo[5.4.0]undec-7-ene (DBU) in DMSO also successfully provided Polymer 1 with a similar degree of polymerization.

Alternative routes of polymerization were also explored, such as hydrolysis of benzyl bromide (compound 4) followed by a subsequent reaction with adipoyl chloride. Unfortunately, the desired hydrolysis product of 4 could not be isolated.

Synthetic accessibility was observed for Polymer 2 (Scheme 2). Polymer 2 was synthesized according to Scheme 2 which began with the selective protection of 2,6-bis(hydroxymethyl)-p-cresol with tert-butyldimethylsilyl chloride (TBDMSCl) afforded 5 in good yield (95%). The phenol of 5 was then combined with 4-(hydroxymethyl)phenylboronic acid pinacol ester to provide the protected boronic ester 6. Removal of the TBS protecting groups provided monomer 7, which is capable of copolymerization with adipoyl chloride. GPC data showed a higher degree of polymerization for 2 compared to 1 (see, FIG. 2, solid line), which is not unexpected as the polymerization methods are different.

Example 12

Nanoparticles Formulation

To a vial, 25 mg of Polymer 1 or Polymer 2 was added and solubilized with 2.5 mL of CH$_2$Cl$_2$. Nile Red (0.5 mg) in 0.5 mL of CH$_2$Cl$_2$ was added to the polymer solution. Then, the solution was added to 50 mL of 1% polyvinyl alcohol (PVA)

in PBS aqueous buffer solution. For 10 min, the solution was stirred at 1000 rpm using a magnetic stirrer.

To achieve further emulsification, a high pressure homogenizer (Microfluidic 110PS, USA) was utilized at 23000 psi for three cycles. Afterwards, the solution was stirred at room temperature at 1000 rpm to evaporate $CH_2Cl_2$ overnight. In order to remove unencapsulated Nile red (solubility in aqueous media<1 µg/mL) (Greenspan, P.; Fowler, S. D. J. Lipid Res. 1985, 26, 781-789) and wash out PVA, the solution was passed through a 1 µm syringe filter (Millipore) and then through a concentrated mode tangential flow filtration system using 500 kDa Pellicon XL cassettes (Millipore, USA).

The nanoparticle suspension was washed with 3 portions of $H_2O$ (50 mL) and concentrated to 8 mL. Prior lyophilization, 240 mg Trehalose was added to the suspension. Overall yield for the nanoparticles synthesis is expected to be around 100% for two reasons: (1) The procedure followed here has been already used in several published articles of the group and it is shown not to form nanoparticles larger than 1 µm; and (2) This process eliminates all steps that could cause loss of particles having sizes smaller than 1 µm.

In contrast to spinning down of the nanoparticles, in the tangential flow filtration system used here, the particle suspension passes over a 500 kDa membrane and, therefore, all particles larger than 40 nm in size are recovered.

Example 13

Nanoparticle Characterization

Polymer 1 and Polymer 2 were formulated into nanoparticles via an oil/water emulsion technique. Scanning electron microscopy (SEM) and dynamic light scattering (DLS) analysis indicated the formation of nanoparticles with an average size of approximately 150 nm (see, FIG. 3A and FIG. 3B).

Example 14

Evaluation of Controlled Release

Polymer 1 and Polymer 2 were formulated into nanoparticles encapsulating a solvatochromic dye, Nile red, to monitor hydrogen peroxide-triggered release from these polymeric nanoparticles. The encapsulation efficiency was determined by fluorescence and HPLC (50% and 44%, respectively).

The fluorescence of the dye was quenched in aqueous environments, enabling use as a model compound to indicate small molecule release from the hydrophobic nanoparticle interior. Prior to the evaluation of controlled release from our materials, the stability of Nile Red fluorescence in hydrogen peroxide was tested to ensure that the fluorescence quenching observed is not a result of Nile Red exposure to hydrogen peroxide. Nile Red fluorescence did not change significantly over the course of 72 h of incubation with the highest hydrogen peroxide concentration used in our study (1 mM).

Figures 4A, 4B:
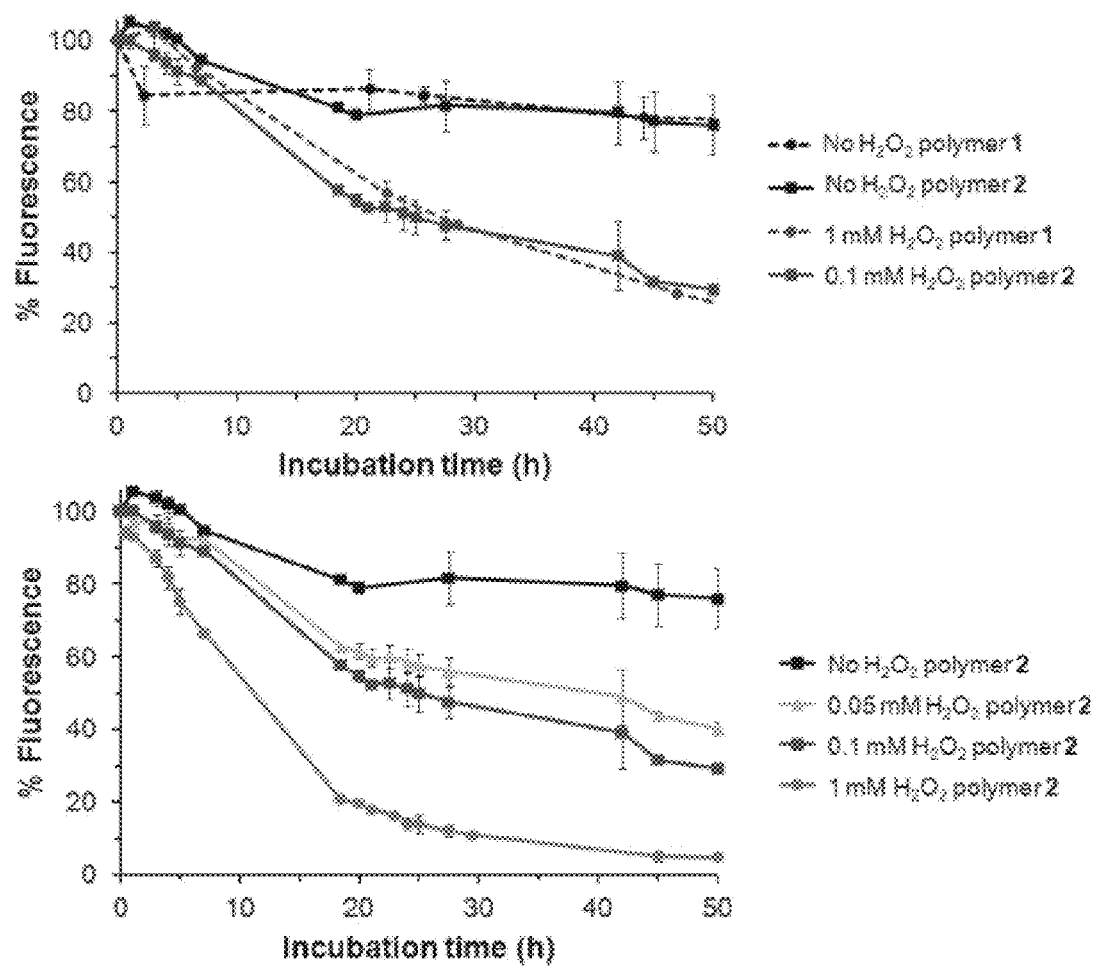
FIG. 4A and FIG. 4B are plots of the fluorescence of Nile red upon release from nanoparticles in PBS (pH 7.4) of Polymer 1 and Polymer 2, respectively, in the absence or presence of various concentrations of hydrogen peroxide, as a function of an incubation time at 37° C.

Exposure to 1 mM $H_2O_2$ (in PBS, pH=7.4) decreased the fluorescence intensity of Nile red in both nanoparticle formulations (see, FIG. 4A (Polymer 1) and FIG. 4B (Polymer 2)). A red shift from around 625 to 640 nm, indicating that the environment of the dye had been altered, was also observed. For nanoparticles prepared using Polymer 1, a 50% decrease in fluorescence is observed at 26 h. This result agrees with our TEM images (see, FIG. 5B) of the degraded empty particles upon exposure to the same $H_2O_2$ concentration (1 mM), which indicate release of the dye.

Because the nanoparticles fall apart, Nile Red is now exposed to a more polar medium, resulting in fluorescence quenching. In the absence of $H_2O_2$, Nile red maintains 80% of its fluorescence at 622 nm over 6 days. This slight decrease may result from quenching of Nile red adsorbed onto the surface of the particles.

Nanoparticles made from Polymer 2, containing an ether linkage, degraded about an order of magnitude more rapidly in response to peroxide and were similarly stable in the absence of peroxide (See, FIG. 4A). Exposure to 100 µM $H_2O_2$ induced a 50% decrease in Nile red fluorescence for these nanoparticles, while those from Polymer 1 required 1 µM $H_2O_2$ to release to the same degree within 50 hours. Thus, Polymer 2 is sensitive to biologically relevant concentration of $H_2O_2$ (50-100 µM) (see, FIG. 4B).

Exposure to 1 mM $H_2O_2$ resulted in complete quench of the dye within a day. These release kinetics agree with the recent finding (in the context of $H_2O_2$ activated metalloprotein inhibitors) of faster conversion of the boronic ester to the phenol by prodrugs employing an ether linkage than those with a direct linkage.

Example 15

$H_2O_2$ Induced Nanoparticle Degradation

After formation and purification, nanoparticle degradation was investigated using transmission electron microscopy (TEM). Direct visualization by TEM reveals how polymer degradation affects nanoparticle structure. Contrary to indirect methods using light scattering or transmission, direct visualization of the particles morphology by TEM can detail any significant changes in the morphology of the nanoparticles after treatment with $H_2O_2$.

Representative particles are presented in FIG. 3A, FIG. 3B and FIGS. 5A-D. Additional TEM images of particles in the absence and presence of varied concentrations of $H_2O_2$ (250 mM, 100 mM, 100 µM, and 50 µM) are presented in FIGS. 11-20.

Figures 5A, 5B, 5C, 5D:
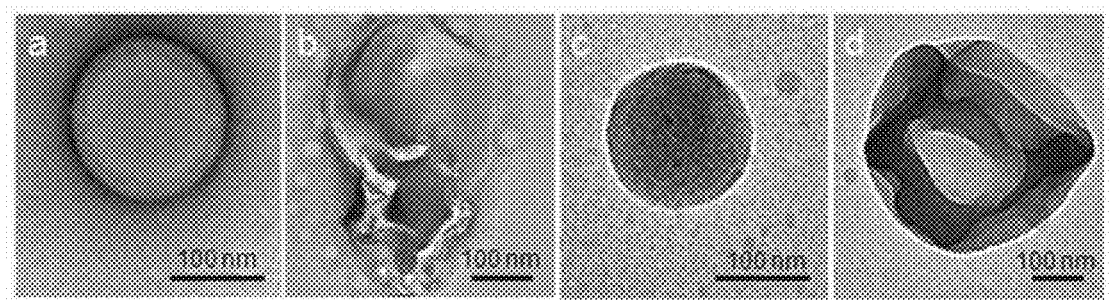
FIGS. 5A to 5D are exemplary TEM images of Polymer 1 nanoparticles (5A, 5B) and Polymer 2 nanoparticles (5C, 5D), according to one embodiment. Specifically.

Almost all nanoparticles are spherical and intact in the absence of $H_2O_2$ (see, FIG. 5A (Polymer 1) and FIG. 5C (Polymer 2)). Exposure to 1 mM hydrogen peroxide induces significant ripping or crumpling of the structures, as well as particle expansion, in most particles (see, FIG. 5B (Polymer 1) and FIG. 5D (Polymer 2).

Similar morphological changes were observed for nanoparticles of Polymer 1 and nanoparticles of Polymer 2 in the presence of 100 mM (3 min) or 250 mM (10 min), but the ratio between intact and degraded was much more balanced. Interestingly, for nanoparticles of Polymer 2, this combination of intact and degraded particles was also observed at low concentrations of $H_2O_2$ (100 µM and 50 µM). This supports the conclusion that physiological concentration of peroxide induces the degradation of Polymer 2.

Example 16

Particle Payload Release with and without Activating ROS Production in Neutrophils Activated neutrophils generate high ROS. Extracellular hydrogen peroxide produced by neutrophils (differentiated mouse promyleocytes or dMPRO cells) with and without PMA (phorbol 12 myristate 13 acetate) stimulation was measured.

After 6 h of PMA treatment, $1.6 \times 10^6$ dMPRO cells produced 6.5 µM $H_2O_2$, while untreated cells produced 4.5 µM $H_2O_2$. These extracellular levels of $H_2O_2$ were much lower than the levels previously seen for Polymer 2, however the concentration of $H_2O_2$ inside neutrophil granules appear to be much higher. Fluorescein diacetate (FDA), a non-fluorescent molecule which is cleaved to fluorescein (Ex490/Em520) by cellular esterases, was chosen for the release assay.

FDA encapsulated in nanoparticles fabricated from Polymer 2, from PLGA and from a control polymer similar in structure to Polymer 2 (with a protecting group that does not cleave in the presence of ROS) were added to PMA treated and untreated dMPRO cells and fluorescence was measured at different time points (0.5, 2 and 6 h).

Figure 6:
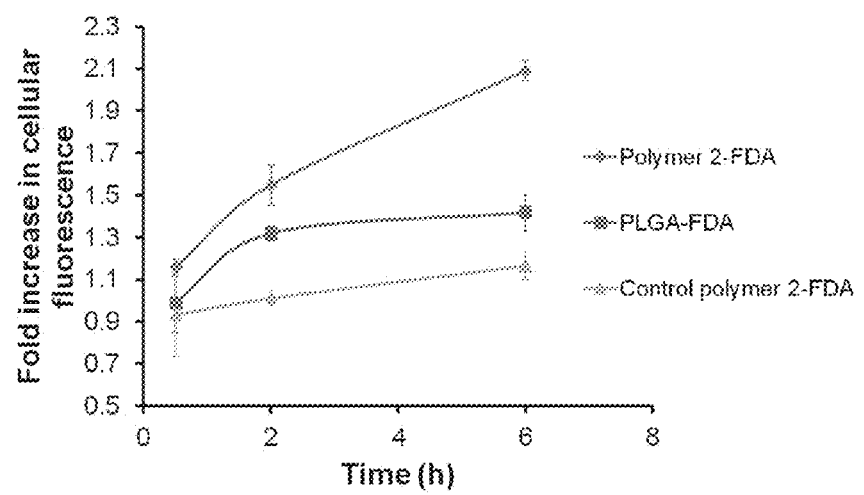
FIG. 6 is a plot of fold increase in cellular fluorescence after PMA stimulation after 0.5, 2 and 6 h, according to one embodiment.
Figure 7A:
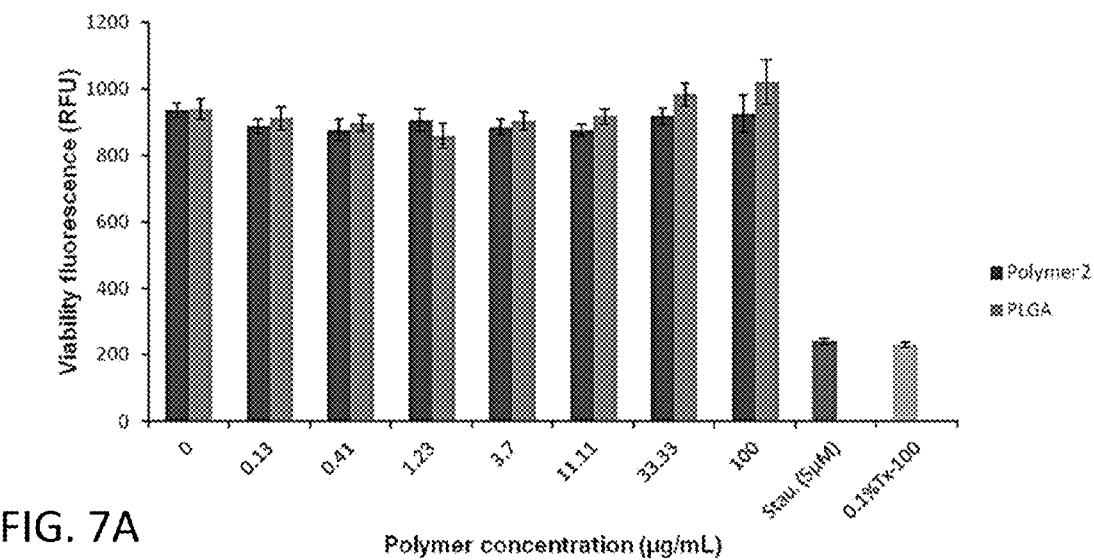
FIGS. 7A to 7C are graphs of the cytotoxicity analysis for viability, cytotoxicity, and apoptosis, respectively, of the $H_2O_2$ degradable nanoparticles from Polymer 2 and PLGA nanoparticles incubated for 5 hrs at different concentrations with Raw 264.7 cells using Apotoxglo assay, according to one embodiment.
Figure 7B:
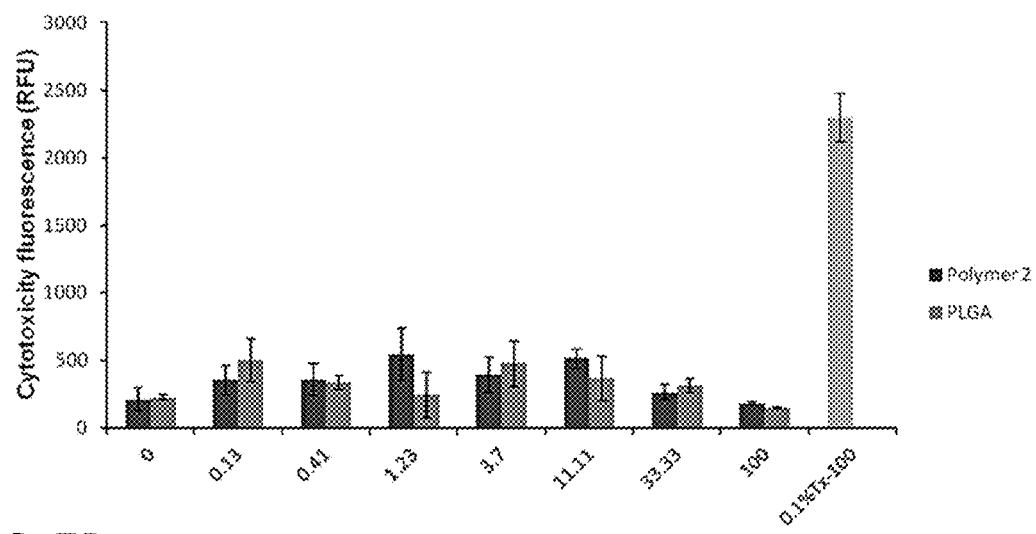
Figure 7C:
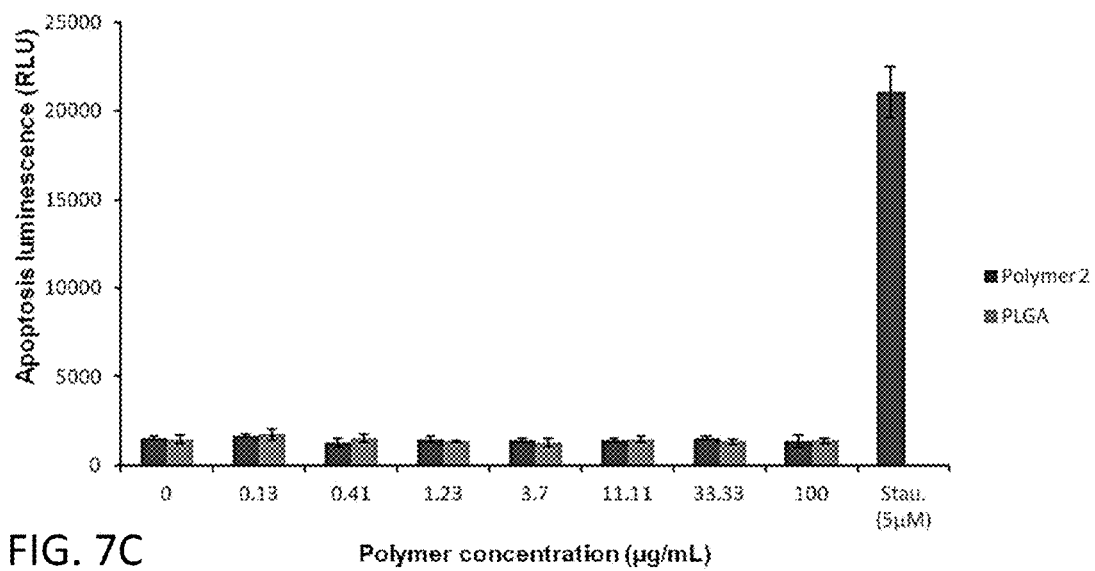
Figure 7D:
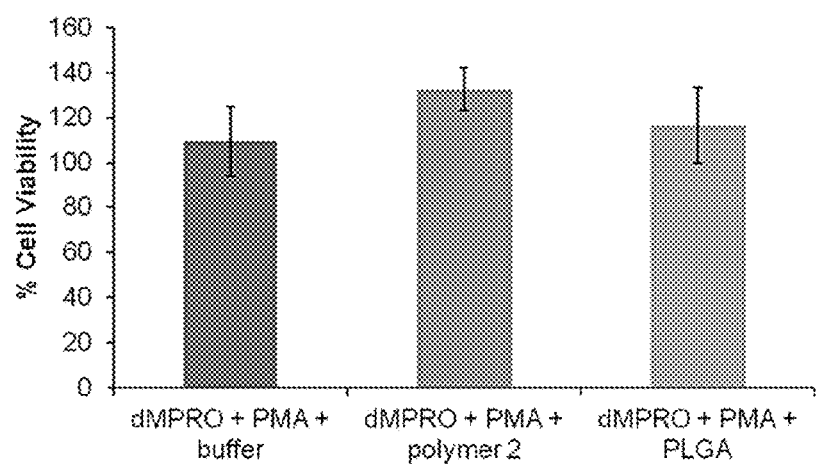
FIG. 7D is a graph of the percent cell viability of phorbol 12 myristate 13 acetate (PMA)-stimulated differentiated promyelocytes (dMPRO) after incubation in buffer, Polymer 2 nanoparticles and PLGA for 4 h, according to one embodiment.
Figures 13A, 13B, 13C, 13D:
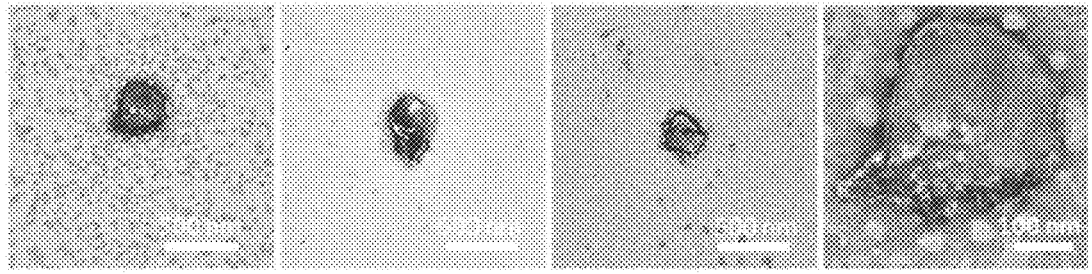
Figures 14A, 14B, 14C, 14D:
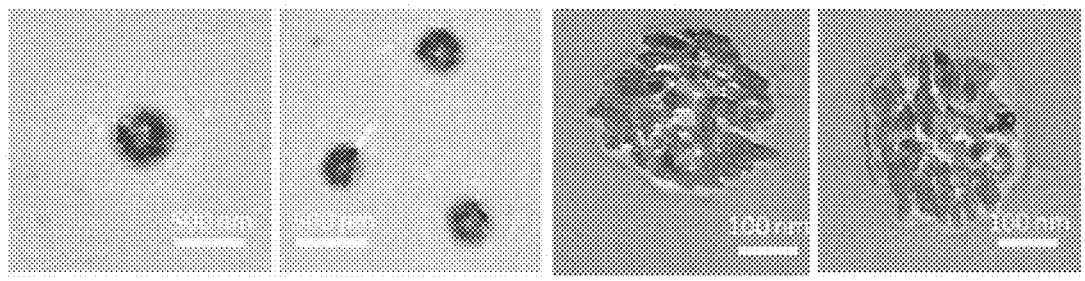

Release of FDA was calculated as the ratio of fluorescence from PMA treated to untreated cells. FIG. 6 shows the fold increase in cellular fluorescence after PMA stimulation after 0.5, 2 and 6 h). Overall a two fold increase in release of FDA from nanoparticles of Polymer 2 was observed in stimulated dMPRO cells while PLGA showed no further release after the initial burst release observed in the first 2 h period. Nanoparticles from control Polymer 2 showed a non-specific response.

Example 17

Cytotoxicity of Nanoparticles from Polymer 2

As nanoparticles from Polymer 2 could provide ROS controlled cargo release upon exposure to biologically relevant oxidative conditions, we tested their cytotoxicity by Apotoxglo assay, which measures live and dead cell protease activity to assess viability and cytotoxicity, respectively.

In addition, this assay also measures caspase 3/7 activity as a readout for apoptosis (see, FIGS. 7A-7D). We compared the effect of these nanoparticles on Raw264.7 macrophages with that of the nontoxic FDA-approved polymer poly(lactic-co-glycolic acid) (PLGA) nanoparticles. Staurosporine and 0.1% Triton-X 100 were used as positive controls for induction of apoptosis and cell death, respectively.

No significant differences were observed between PLGA and Polymer 2 nanoparticles up to a concentration of 100 μg/mL (p>0.05). Upon incubation for three different time intervals (5 h, 24 h and 48 h), neither Polymer 2 nor PLGA induced any significant toxicity (cell death or apoptosis) compared to untreated cells (see, FIGS. 7A-7D). On the other hand, apoptosis and loss of cell viability was observed in cells treated with staurosporine and 0.1% Triton X-100 (see, FIGS. 7A-7C).

To test if Polymer 2 nanoparticles affect viability of activated neutrophils (which would mimic pathological conditions in vivo), we incubated Polymer 2 and PLGA nanoparticles for 4 h with activated neutrophils (phorbol 12 myristate 13 acetate-stimulated dMPRO cells). Cell viability post-incubation was measured by trypan blue staining; no loss in cell viability was seen in either case (see, FIG. 7D).

Example 18

Polymer Degradation

After validating that degradation of Polymer 2 at biologically relevant oxidative levels initiates payload release, degradation was characterized by GPC and NMR. High concentrations of $H_2O_2$ were used to fully degrade the polymers and confirm that the polymers degrade into predicted products.

The degradation of Polymer 1 was examined in 250 mM $H_2O_2$ in a 20% PBS/DMF (v/v) solution by gel permeation chromatography (GPC) and NMR. FIG. 8A and FIG. 8B show $^1$H NMR spectra of Polymer 1 in DMSO-$d_6$, deuterium PBS without $H_2O_2$ (see FIG. 8A) and incubated with 500 mM $H_2O_2$ after 46 h at 37° C. (see FIG. 8B). Solvent peaks (s) include DMSO-$d_6$, $D_2O$ and traces of water, ethyl acetate, methanol and dichloromethane. FIG. 8C shows GPC chromatograms of the polymer prior to the addition of $H_2O_2$ (solid line) and after degradation in 20% PBS/DMF solutions containing 250 mM $H_2O_2$ incubated at 37° C. (dotted line). (1*protected and de-protected polymer.)

GPC following 66 h exposure to peroxide revealed small molecule peaks corresponding to products of degradation of polyester 1, adipic acid and 2,6-bis(hydroxymethyl)phenol (cresol) (Scheme 1) that constitute 35% of the peak area (see, FIG. 8C). The chemical composition of the small molecule products was confirmed by NMR (see, FIG. 8B). As the rate of polymer degradation depends on $H_2O_2$ concentration, high concentrations of $H_2O_2$ (500 mM) were used. NMR peak shifts corresponding to the formation of cresol and the liberation of adipic acid were observed; the ester bonds of the polymer degrade to carboxylic acids and alcohols. The benzyl proton peaks shift from 5.03 to 4.54 ppm, indicating a change from the ester to the benzyl alcohol. Furthermore, protons alpha to the ester carbonyl shifted from 2.28 to 2.16 ppm, corresponding to protons of adipic acid.

NMR shows clear evidence that the target degradation products are formed. However, chemical shifts from the remaining polymer, both protected and deprotected, are still observed by NMR (at 46 h) and by GPC (at 66 h), indicating that degradation into small molecules or oligomers is not complete in the time frame investigated. Polymer 1 thus has slow and incomplete degradation. However, this result is not unexpected, as conversion of the boronic ester to the phenol using a direct linkage strategy is slow. However, when formulated into nanoparticles, TEM and Nile Red release experiments showed that the observed polymer degradation could translate into sufficient particle degradation to result in release of an encapsulated payload.

Degradation of Polymer 2 was quantified as for 1, first by $^1$H NMR, in the absence of $H_2O_2$ or with 50 mM $H_2O_2$. As shown in FIGS. 9A-9B, complete degradation occurred within 3 days, as broad peaks corresponding to the polymer have been replaced by the sharp peaks of the degradation products. Contrary to what it has been found for 1, $H_2O_2$ driven, almost complete and fast degradation was found for 2, and this with at least one order of magnitude less $H_2O_2$ concentration.

GPC analysis (see FIG. 9D) showed that Polymer 2 depolymerized upon only 24 h of $H_2O_2$ at 50 mM exposure. In agreement with the previous NMR result, the polymer degraded completely after 3 days at this concentration. Interestingly, GPC reveals degradation started even with a biologically relevant $H_2O_2$ concentration (100 μM, green line). Importantly, neither 1 nor 2 are hydrolyzed in the absence of $H_2O_2$ (tested over 6 days).

Example 19

GPC Analysis of Polymer Degradation

Polymer 1 (23.5 mg) was dissolved in a mixture of 1.625 mL of DMF/PBS (pH 7.4) 80/20. 0.3 mL of the solution was taken in two different vials. To one vial, 8.5 μL of $H_2O_2$ (30%) was added (250 mM) before placing them in an incubator at 37° C. After 66 h of incubation, the solutions were evaporated to dryness. 25 μL DMF (containing 0.01% LiBr) was added and the filtered solutions were injected into the GPC instrument.

Four Polymer 2 solutions were prepared by dissolving 6 mg of Polymer 2 in a mixture of 1.625 mL of DMF/PBS (pH 7.4) 80/20. $H_2O_2$ was added to reach 100 mM, 50 mM, 1 mM or 100 µM. 137 µL aliquots were taken after 24 h, 2, 3 and 6 days and evaporated to dryness. 300 µL DMF (containing 0.01% LiBr) was added and 20 µL of the filtered solutions were injected into the GPC instrument. Neither Polymer 1 nor Polymer 2 showed significant hydrolysis in the absence of $H_2O_2$ (tested over 6 days).

Example 20

NMR Analysis of Polymer Degradation Products

To Polymer 1 (13.6 mg), 0.8 mL of DMSO-$d_6$ was added, followed by the addition of a deuterated PBS (pH 7.4) (143 µL) buffer solution. To dissolve the precipitate, 50 µL of $D_2O$ and 250 µL of DMSO-$d_6$ was added. The solution was transferred to a NMR tube. 70.4 µL of $H_2O_2$ was added to make a 0.5 M solution and the tube was incubated at 37° C. $^1H$ NMR spectra was acquired at various time points.

To Polymer 2 (5 mg), 0.3 mL of DMSO-$d_6$ was added, followed by the addition of a deuterated PBS (pH 7.4) (80 µL) buffer solution. The solution was transferred to a NMR tube and incubated at 37° C. To the solution, 20 µL of $H_2O_2$ was added to make a 50 mM solution.

Example 21

Fluorescence Analysis of Nile Red Release

Nanoparticles 1 (11.4 mg) were added to a vial and dissolved in 6 mL of PBS aqueous buffer (pH=7.4) and filtered through a 1 µm syringe filter. 1 mL of the nanoparticle solution was added into 3 different quartz cuvettes. $H_2O_2$ (10 µL, 100 mM) was added to each. For samples with no $H_2O_2$ added, 10 mg of nanoparticles were dissolved in 5 mL of PBS aqueous buffer. The solution was filtered through a 1 µm syringe filter and 1 mL was added to each of 3 quartz cuvettes.

The solutions were then incubated at 37° C. Nanoparticles 2 (3 mg) were dissolved in 4.5 mL of PBS aqueous buffer (pH=7.4). 1 mL aliquots were further diluted by adding 1.970 mL of PBS. $H_2O_2$ was added to 3 of the 4 vials to reach 50 µM, 100 µM or 1 mM and the solutions incubated at 37° C. Fluorescence measurements (3 replicates) were taken at various time points over a period of days using the same instrument settings as reported previously.

Example 22

Effect of $H_2O_2$ on the Fluorescence Activity of Nile Red

Nile red solutions of three different concentrations in acetone were prepared (10, 40, 160 ng/mL). Polymer 1 was dissolved in the Nile red solutions (polymer concentration in all Nile red solutions were constant at 125 µg/mL). Hydrogen peroxide was added to these solutions (concentration in Nile red solutions was constant at 1 mM). Changes in Nile red fluorescence were monitored over a 72 h period using the same instrument settings as reported previously. These experiments were run in duplicate.

Example 23

Imaging of Nanoparticles by SEM

Lyophilized empty particles were suspended in MilliQ $H_2O$ at 2 mg/mL, vortexed, and sonicated. Then, further diluted 10-fold and dropped on a cleaned Si wafer piece. The droplet was dried under vacuum for 30 min. Approximately 15 nm of chromium was deposited on the chips by sputter coating. Particles were imaged directly using a FEI XL30 Ultra High Resolution SEM.

Example 24

Imaging of Nanoparticles by TEM

Lyophilized empty particles were resuspended by adding water. The resulting solution was filtered through a 0.45 µm filter (PALL Life Sciences, NY). 1% and 0.5% phosphotungstic acid (PTA) solution, pH 7.4, was prepared. Copper grids, 400 mesh, with a carbon film on only side were purchased from Electron Microscopy Sciences (Hatfield, Pa.); grids were glow discharged prior to use.

Particle solutions were prepared at the determined $H_2O_2$ concentrations, and either 3.5 µl of the solution was immediately placed on the grid, or incubated at 37° C. for 72 h, 10 or 3 min and then placed on the grids. After 10 min, grids were rinsed with water, then PTA solution (1% for particles 1, 0.5% for particles 2), and the resulting liquid was wicked away with filter paper. Grids were then stored until imaging at ambient conditions. A FEI Spirit TEM was used at 120 kV to image particles.

Example 25

Release Assay in Neutrophils

Fluorescein diacetate (FDA) containing nanoparticles (polymer 2, PLGA and control polymer 2) were resuspended in Hank's buffered salt solution (HBSS) supplemented with 0.1% glucose and added to $1 \times 10^6$ dMPRO cells (per 100 µL, in HBSS) to give a final concentration of 1 µg/mL FDA.

One set of cells incubated with nanoparticles were left untreated while a second identical set was stimulated to produce ROS by addition of Phorbol-12-myristate, 13-acetate (PMA, 3.2 µM final concentration). After particle addition (and +/−PMA treatment), the cells were incubated at 37° C. for 0.5, 2 and 6 h. At each time point, the cells were pelleted, re-suspended in PBS and fluorescein emission (520 nm) was measured. Release of FDA was calculated as fold increase in fluorescence of PMA treated cells to untreated cells. Each point in dataset was measured in triplicates.

Example 26

Measurement of Viability, Cytotoxicity and Apoptosis

Raw264.7 cells were seeded on a 96-well plate at a density of 15000 cells per well. Twenty four hours post-incubation, cell culture medium was replaced by a medium containing nanoparticle suspension (PLGA or Polymer 2, 0-100 µg/mL). The particles were incubated for 5, 24 and 48 h.

Apoptosis (positive control) was induced by addition of staurosporine (5 µM final concentration), followed by incubation for at 37° C. for 5 h. Cytotoxicity (positive control) was induced by addition of triton X-100 (0.1% final concentration), followed by incubation at 37° C. for 15 min. Viability, cytotoxicity and apoptosis were measured using ApoTox-Glo™ assay (Promega) as per manufacturer's protocol. Datasets for each concentration and controls were collected in quadruplicates.

Example 27

Measurement of Viability During Active ROS Production in Presence of Nanoparticles Differentiated MPRO cells ($5.5 \times 10^5$ per 100 μL) were stimulated with PMA (3.2 μM final concentration). Immediately after PMA addition, nanoparticle suspension (PLGA or Polymer 2, final concentration 100 μg/mL) or an equal volume buffer (negative control) was added, followed by incubation at 37° C. for 4 h. Cell viability was measured by trypan blue exclusion using a TC-10 cell counter. Datasets for Polymer 2, PLGA and control were collected in quadruplicates.

Example 28

Nile Red Encapsulation Efficiency (EE) Determined by Red Fluorescence

Nanoparticles 2 encapsulating Nile red were dissolved in a mixture of acetone:$H_2O$ (95:5) to release Nile red into the solution. Nile red fluorescence intensity was measured (excitation at 531 nm, emission at 612 nm) and the amount of dye encapsulated was determined according to the calibration curve presented in FIG. 21A.

All calibration curves were obtained by measuring fluorescence of various concentrations of Nile red in acetone. Linear regression of peak area versus concentration yielded the curve.

Example 29

Nile Red Encapsulation Efficiency (EE) Determined by HPLC

The amount of Nile red was also evaluated using a HPLC-UV-Vis system and detected by absorption at 559 nm as reported in the literature. Nanoparticles 2 were dissolved in a mixture of acetone:$H_2O$ (95:5). In order to isolate the dye from the polymer, the solvents were removed under vacuum. Then, methanol was added to the residue and the polymer spun down by centrifugation. Finally, aliquots of supernatant were injected into the HPLC (mobile phase: isocratic methanol:$H_2O$ (93:7), flow rate maintained at 0.2 mL/min).

Example 30

Nanoparticles Encapsulating Paclitaxel—Formulation

Paclitaxel (1 mg) and Polymer 2 (100 mg) were solubilized in 5.0 mL of $CH_2Cl_2$. Then the solution was added to 50 mL of 1% PVA in water and stirred at 1000 rpm using a magnetic stirrer for 2 min. To achieve further emulsification, a high pressure homogenizer (Microfluidic 110PS, USA) was utilized at 23000 psi for three cycles. Afterwards, the solution was stirred at room temperature at 1000 rpm to evaporate $CH_2Cl_2$.

The solution was passed through a 1 μm syringe filter (Millipore) and then through a concentrated mode tangential flow filtration system using 500 kDa Pellicon XL cassettes (Millipore, USA) against water. 75 mg mannitol was added and the suspension was lyophilized. DLS analysis indicated the formation of nanoparticles with an average size of approximately 150 nm (PDI=0.21). Encapsulation efficiency was determined to be 33% by dissolving particles in acetone and quantifying paclitaxel by LC-MS. (see, FIG. 22)

Example 31

Nanoparticles Encapsulating Paclitaxel—Release 25 mg of particles were suspended in PBS (pH 7.4, 1×), containing either 1 mM or 50 μM $H_2O_2$ and incubated at 37° C. for 2 or 3 days. After centrifugation (25 min, 4,750 rpm), the supernatant (80% by volume) was extracted twice with $CH_2Cl_2$. After drying, the residue was dissolved in acetonitrile, filtered (0.45 μm) and injected into the LC-MS column. Paclitaxel was quantified by comparison to the calibration curve presented in FIG. 23.

Comparative payload release (Paclitaxel and Nile red) as determined by LCMS or fluorescence is presented below in Table 1:

TABLE 1

| $[H_2O_2]$ | % Paclitaxel release determined by LCMS (incubation time) | % Nile red release determined by fluorescence (incubation time) |
|---|---|---|
| PBS only | 23 (48 h) | 20 (50 h) |
| 50 μM | 63 (72 h) | 50 (50 h) |
| 1 mM | 97 (48 h) | 95 (50 h) |

Example 32

Formulation of Nanoparticles Encapsulating FDA

Particles were prepared using 0/W method. Fluorescein diacetate (FDA) in DMSO (37.5 μA 50 mg/mL stock) was added to 262.5 μl DCM containing 10 mg polymer (either Polymer 2, Control Polymer 2 (light sensitive polymer) or PLGA (75:25, MW=76,000-115,000)). Then 6 mL 1% PVA in PBS pH 7.4 was added.

The mixture was sonicated using ⅛" probe sonicator (power of 8, Misonix S-4000, USA) for the emulsion to be stable (4-9 min). The DCM was left to evaporate under stirring and the particles were washed with water using the tangential flow setup as previously described. Finally the particles were lyophilized in the presence of 100 mg Trehalose.

The amount of encapsulated FDA was determined by mixing the aqueous nanoparticles solution with equal volume of DCM followed by the addition of 0.1N NaOH to hydrolyse the diacetate and generate the fluorescence. The results are provided in Table 2 below:

TABLE 2

|  | Z-average (nm) | PDI | EE (%) |
|---|---|---|---|
| Polymer 2 | 243.3 | 0.145 | 6 |
| Control Polymer 2 | 297.2 | 0.299 | 5.3 |
| PLGA | 187.3 | 0.096 | 3.4 |

Example 33

Magneto-Luminescent (MRI/NIR) ROS Sensor

The encapsulation of a gadolinium (Gd) chelate-near infrared (NIR) dye conjugate (See FIG. 25) within electrosprayed nanoparticles consisting of the ROS-responsive polymer, resulted in a magneto-luminescent (MRI/NIR) ROS sensor.

The ability of the Gd chelate to relax surrounding water molecules is silenced by encapsulation in the polymer; the NIR fluorescent signal is also quenched by energy transfer to adjacent dye molecules. ROS-triggered release activates both signals by enabling Gd chelates to interact with water and releasing dye self-quenching.

The resulting "OFF-state" sensors are very stable over time; both signals stay low for days at physiological pH, which means that the particles remain intact in the absence of $H_2O_2$ activation. However, increasing amounts of $H_2O_2$ (as low as 100 μM) trigger increasing degradation of the polymer, which generates a corresponding dual increase in $T_1$ relaxation rates (See FIG. 26A) and fluorescence (See FIG. 26B). This dual imaging system is sensitive to the quantities of $H_2O_2$ produced by phorbol 12-myristate 13-acetate-activated dMPRO cells (See FIG. 26C).

Example 34

Release of Dexamethasone in Response to Induced In Vivo Inflammation

To examine whether the $H_2O_2$-responsive polymer could be used to deliver anti-inflammatory drugs to sites of inflammation, nanoparticles composed of this polymer and encapsulating dexamethasone (dex) were injected directly into inflamed paws (inflammation induced by carrageenan injection). Therapeutic effects, as indicated by paw volume measured by plethysmometer, were compared to free dex delivered intraperitoneally, empty $H_2O_2$-responsive particles, and dexamethasone delivered locally in non-responsive particles composed of poly(lactic-co-glycolic acid) (PLGA), with PBS and empty PLGA particles as negative controls. Equal concentrations of dex, as determined by LC-MS of prepared nanoparticles, were injected.

Dex delivered in the $H_2O_2$-responsive polymer alleviated carrageenan-induced paw inflammation at 3, 5, and 8 h post-injection (See FIG. 27) (p<0.001 compared to vehicle). However, reductions in swelling caused by dex in this formulation were similar to those caused by locally delivered dex at 5 and 8 h, and were considerably smaller than those caused by intraperitoneally delivered free dex at 8 h.

Example 35

Delivery of VEGF-Trap in Oxygen Stress-Triggered Neovascularization

Because treatment of neovascular (exudative or "wet") age-related macular degeneration (AMD) using anti-VEGF biologics requires frequent intravitreal injections, we hope to incorporate the $H_2O_2$-responsive polymer into a formulation to extend the lifetime of each injection. Generation of ROS on the macula caused by drusen accumulation is thought to contribute to progression, so an ROS-responsive vehicle could enable release of drug when it's most needed.

In preliminary studies, the therapeutic efficacy of VEGF-Trap, a fusion protein consisting of VEGFR1 and VEGFR2 domains attached to the Fc region of IgG, delivered in $H_2O_2$-responsive polymer nanoparticles was compared to that of a dose of free VEGF-Trap. Both were administered intravitreously in a neonatal retinopathy of prematurity (ROP) mouse model, and the extent of neovascularization was examined 5 days later. VEGF-Trap delivered in responsive nanoparticles was as effective as free VEGF-Trap in reducing neovascularization (See FIG. 28A and FIG. 28B, nanoparticle formulation vs. PBS control).

In addition, release from $H_2O_2$-responsive particles has been compared to that from PLGA in the laser-induced choroidal neovascularization mouse model using a fluorescent dye and observed that responsive particles release more payload.

CONCLUSION

In conclusion, a bioresponsive polyester has been synthesized bearing boronic ester triggering groups that degrade upon exposure to low concentrations of $H_2O_2$. The degradation is induced by transformation of a boronic ester to a phenol, which undergoes a quinione methide rearrangement to break down the polyester backbone. Nanoparticles formulated from the polymer degrade and release contents upon exposure to 50 μM $H_2O_2$. Advantages of our system are good synthetic accessibility and hydrolytic stability, fast $H_2O_2$ triggered cleavage kinetics, good biocompatibility, and the formation of only small degradation molecules that should be easily cleared by the body.

Polymer 2 nanoparticles are used to deliver small molecules or ROS-quenching enzymes such as catalase and superoxide dismutase to treat chronic inflammatory diseases. These diseases, such as chronic obstructive pulmonary disease (COPD) and rheumatoid arthritis, are associated with increased neutrophil recruitment. Degranulation of neutrophils and macrophages produces ROS, which contributes to tissue damage. Thus, using these nanoparticles to deliver drugs that inhibit neutrophil recruitment to sites of chronic inflammation could limit such damage. Anti-neutrophil recruitment drugs include reparixin and SB 225002 (N-(2-hydroxy-4-nitrophenyl)-N'-(2-bromophenyl)urea), which act on the neutrophil chemokine receptor (CXCR2) and inhibit neutrophil migration.

Cytotoxicity analysis of Polymer 2 nanoparticles indicates that these are well-tolerated by both macrophages and stimulated neutrophils. In rheumatoid arthritis, Polymer 2 nanoparticles are injected directly into the joint cavity, while for COPD, nanoparticle administration would likely involve a nebulizer. Ongoing investigations are dedicated to investigating the potential of these polymeric systems to deliver therapeutic and diagnostic agents specifically to tissues undergoing oxidative stress.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, this application controls.

What is claimed is:

1. A pharmaceutical composition comprising a nanoparticle comprising a polymer having the structure

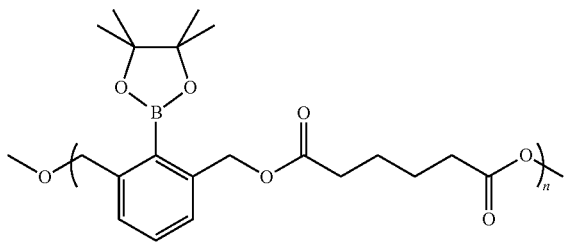

or

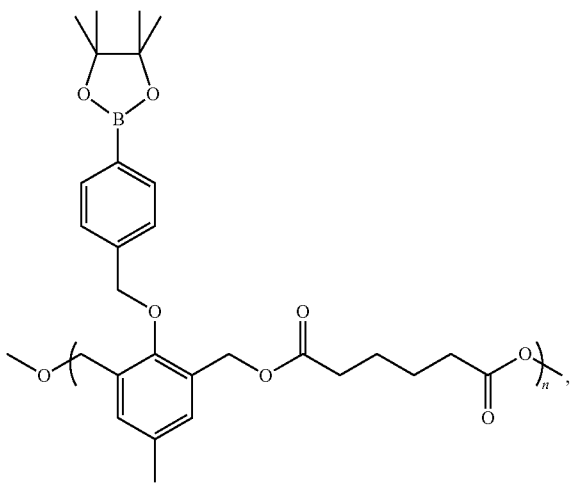

where n is a whole integer between 15-20 and 75-100, respectively;
   at least one active ingredient; and
   at least one pharmaceutically-acceptable excipient.

2. The pharmaceutical composition of claim 1, wherein the polymer is

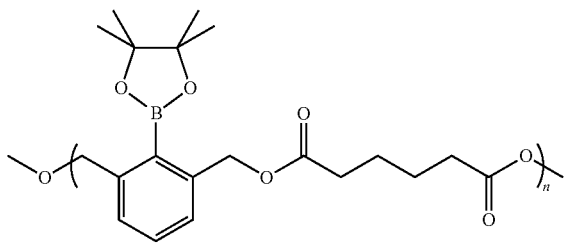

and has a molecular weight between about 10000 and 12000.

3. The pharmaceutical composition of claim 2, wherein the polymer has a polydispersity index (PDI) of about 1.9 and the molecular weight is about 10623.

4. The pharmaceutical composition of claim 1, wherein the polymer is

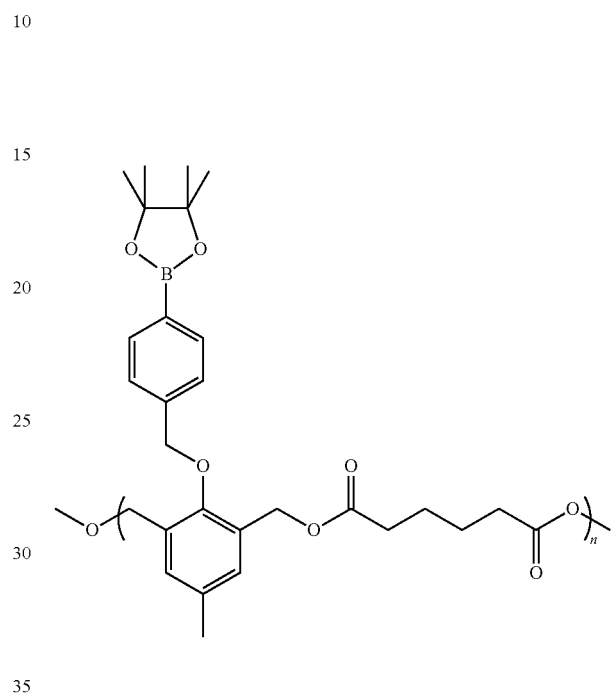

and has a molecular weight between about 50 kDa and 53 kDa.

5. The pharmaceutical composition of claim 4, wherein the polymer has a polydispersity index (PDI) of about 1.4 and the molecular weight is about 51.3 kDa.

6. The pharmaceutical composition of claim 1, wherein the pharmaceutically-acceptable excipient is a thickener, an oil phase, a surfactant, a preservative, or a pH adjusting agent.

7. The pharmaceutical composition of claim 1, wherein the pharmaceutical composition is a solution, emulsion, cream, ointment, lotion, gel, powder, solid, tincture, paste, vapor, tape, or lotion.

* * * * *